(12) United States Patent
Yokosawa et al.

(10) Patent No.: US 10,169,866 B2
(45) Date of Patent: Jan. 1, 2019

(54) MEDICAL IMAGE PROCESSING AND DIAGNOSTIC IMAGE GENERATION DEVICE FOR PREDETERMINED TYPES OF DIAGNOSTIC INFORMATION

(71) Applicant: HITACHI, LTD., Tokyo (JP)

(72) Inventors: Suguru Yokosawa, Tokyo (JP); Yo Taniguchi, Tokyo (JP); Hisaaki Ochi, Tokyo (JP); Toru Shirai, Tokyo (JP); Shinji Kurokawa, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 63 days.

(21) Appl. No.: 15/300,830

(22) PCT Filed: Apr. 22, 2014

(86) PCT No.: PCT/JP2014/061309
§ 371 (c)(1),
(2) Date: Sep. 30, 2016

(87) PCT Pub. No.: WO2015/162694
PCT Pub. Date: Oct. 29, 2015

(65) Prior Publication Data
US 2017/0018080 A1   Jan. 19, 2017

(51) Int. Cl.
| | | |
|---|---|---|
| *G06F 3/0484* | (2013.01) | |
| *G06T 7/00* | (2017.01) | |
| *A61B 5/055* | (2006.01) | |
| *G06T 11/60* | (2006.01) | |
| *A61B 5/00* | (2006.01) | |

(Continued)

(52) U.S. Cl.
CPC ............ *G06T 7/0012* (2013.01); *A61B 5/055* (2013.01); *A61B 5/7435* (2013.01);
(Continued)

(58) Field of Classification Search
CPC ....... A61B 5/055; A61B 5/7435; A61B 6/032; A61B 6/5217; A61B 8/485; A61B 8/5223; G06F 3/04847; G06T 2200/24; G06T 2207/10088; G06T 2207/30004
See application file for complete search history.

(56) References Cited

U.S. PATENT DOCUMENTS

| | | | |
|---|---|---|---|
| 8,643,363 B2 | 2/2014 | Warntjes | |
| 2010/0127704 A1* | 5/2010 | Warntjes | ................ G01R 33/56 324/309 |

(Continued)

FOREIGN PATENT DOCUMENTS

| | | |
|---|---|---|
| JP | 2005-118510 A | 5/2005 |
| JP | 2009-061170 A | 3/2009 |

(Continued)

OTHER PUBLICATIONS

Japanese Office Action received in corresponding Japanese Application No. 2016-514585 dated Aug. 8, 2017.

(Continued)

*Primary Examiner* — Siamak Harandi
(74) *Attorney, Agent, or Firm* — Mattingly & Malur, PC

(57) ABSTRACT

To provide a technique for supporting diagnosis by reducing a user's time and effort in quantitative diagnosis using a quantitative value acquired by a medical image acquisition apparatus. A user is allowed in advance to select only desired diagnostic information from vast amounts of diagnostic information such as images and numerical values. Only the selected diagnostic information is presented to the user in a user-friendly mode. The diagnostic information is calculated by using a physical property value necessary for the calculation of the diagnostic information in question and calculation information such as arithmetic functions and variables, the physical property value and calculation information being stored in advance.

15 Claims, 16 Drawing Sheets

(51) Int. Cl.
 A61B 6/03 (2006.01)
 A61B 6/00 (2006.01)
 A61B 8/08 (2006.01)

(52) U.S. Cl.
 CPC .......... *G06F 3/04847* (2013.01); *G06T 11/60* (2013.01); *A61B 6/032* (2013.01); *A61B 6/5217* (2013.01); *A61B 8/485* (2013.01); *A61B 8/5223* (2013.01); *G06T 2200/24* (2013.01); *G06T 2207/10088* (2013.01); *G06T 2207/30004* (2013.01)

(56) References Cited

U.S. PATENT DOCUMENTS

| | | | | |
|---|---|---|---|---|
| 2011/0060210 | A1* | 3/2011 | Ehman | ............ A61B 5/055 600/410 |
| 2014/0180061 | A1 | 6/2014 | Warntjes | |

FOREIGN PATENT DOCUMENTS

| | | |
|---|---|---|
| JP | 2011-024926 A | 2/2011 |
| JP | 2013-539706 A | 10/2013 |
| WO | 2012/151551 A2 | 11/2012 |

OTHER PUBLICATIONS

International Preliminary Report on Patentability received in corresponding International Application No. PCT/JP2014/061309 dated Nov. 3, 2016.

Sean C.L. Deoni, PhD, "Transverse Relaxation Time (T2) Mapping in the Brain With Off-Resonance Correction Using Phase-Cycled Steady-State Free Precession Imaging", Journal of Magnetic Resonance Imaging 30, 2009, pp. 411-417.

International Search Report of PCT/JP2014/061309 dated Jul. 15, 2014.

* cited by examiner

FIG.3

```
START
  ↓
RECEIVE OUTPUT           — S1101
DIAGNOSTIC INFORMATION
  ↓
ACQUIRE ECHO SIGNAL      — S1102
  ↓
CALCULATE PHYSICAL       — S1103
PROPERTY VALUE
  ↓
CALCULATE DIAGNOSTIC     — S1104
INFORMATION
  ↓
DISPLAY                  — S1105
  ↓
END
```

FIG.4

| DIAGNOSTIC INFORMATION NAME (301) | INPUT PHYSICAL PROPERTY VALUE (302) | CALCULATION INFORMATION (VARIABLE VALUE AND CALCULUS EQUATION (FUNCTION)) (303) |
|---|---|---|
| T1-WEIGHTED IMAGE | T1,T2,PD | .... |
| WHITE MATTER EXISTENCE PROBABILITY MAP | T1,T2 | .... |
| INTENSITY IMAGE OF ABNORMAL TISSUE | T1,T2 | .... |
| VOLUME OF WHITE MATTER | T1,T2,v | .... |
| .... | .... | .... |

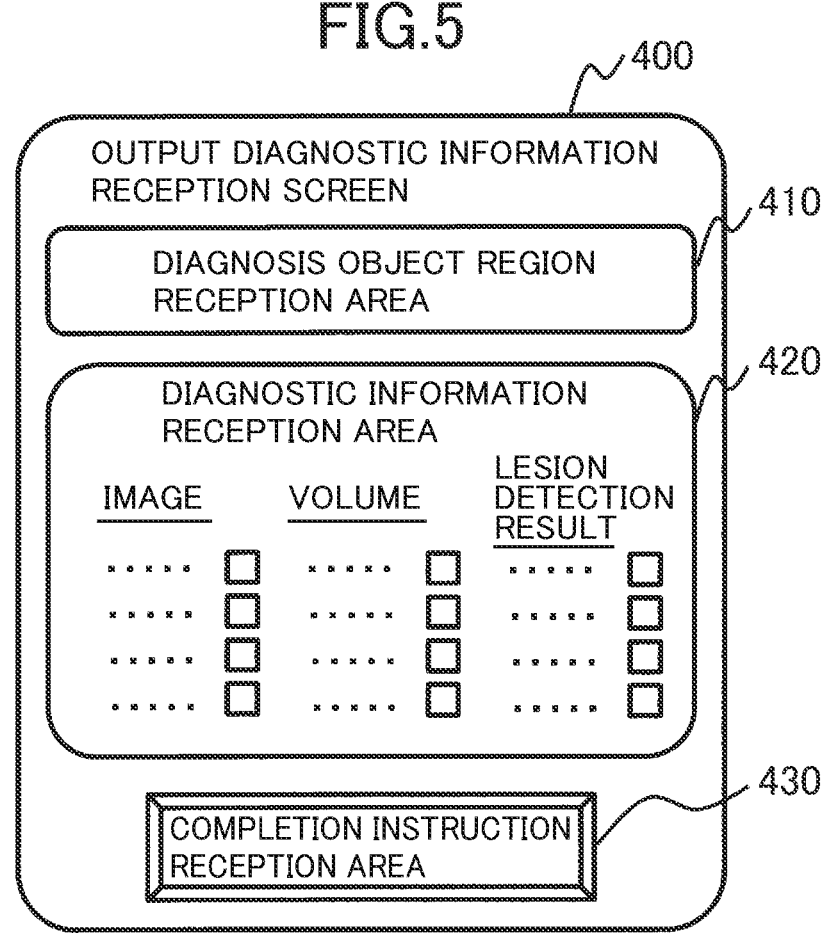

FIG.14

| DIAGNOSTIC INFORMATION NAME | INPUT PHYSICAL PROPERTY VALUE | CALCULATION INFORMATION | IMAGING INFORMATION (PULSE SEQUENCE, TIME) |
|---|---|---|---|
| T1-WEIGHTED IMAGE | T1, T2,PD | ..... | T1WS:3min(UNNECESSARY) SWS:5min(NECESSARY) |
| T2-WEIGHTED IMAGE | T1, T2,PD | ..... | T2WS:3min(UNNECESSARY) SWS:5min(NECESSARY) |
| FLAIR IMAGE | T1, T2,PD | ..... | FWS:3min(UNNECESSARY) SWS:5min(NECESSARY) |
| WHITE MATTER EXISTENCE PROBABILITY MAP | T1,T2 | ..... | ..... |
| INTENSITY IMAGE OF ABNORMAL TISSUE | T1,T2 | ..... | ..... |
| VOLUME OF WHITE MATTER | T1,T2,v | ..... | ..... |
| .... | .... | ..... | ..... |

301    302    303    304

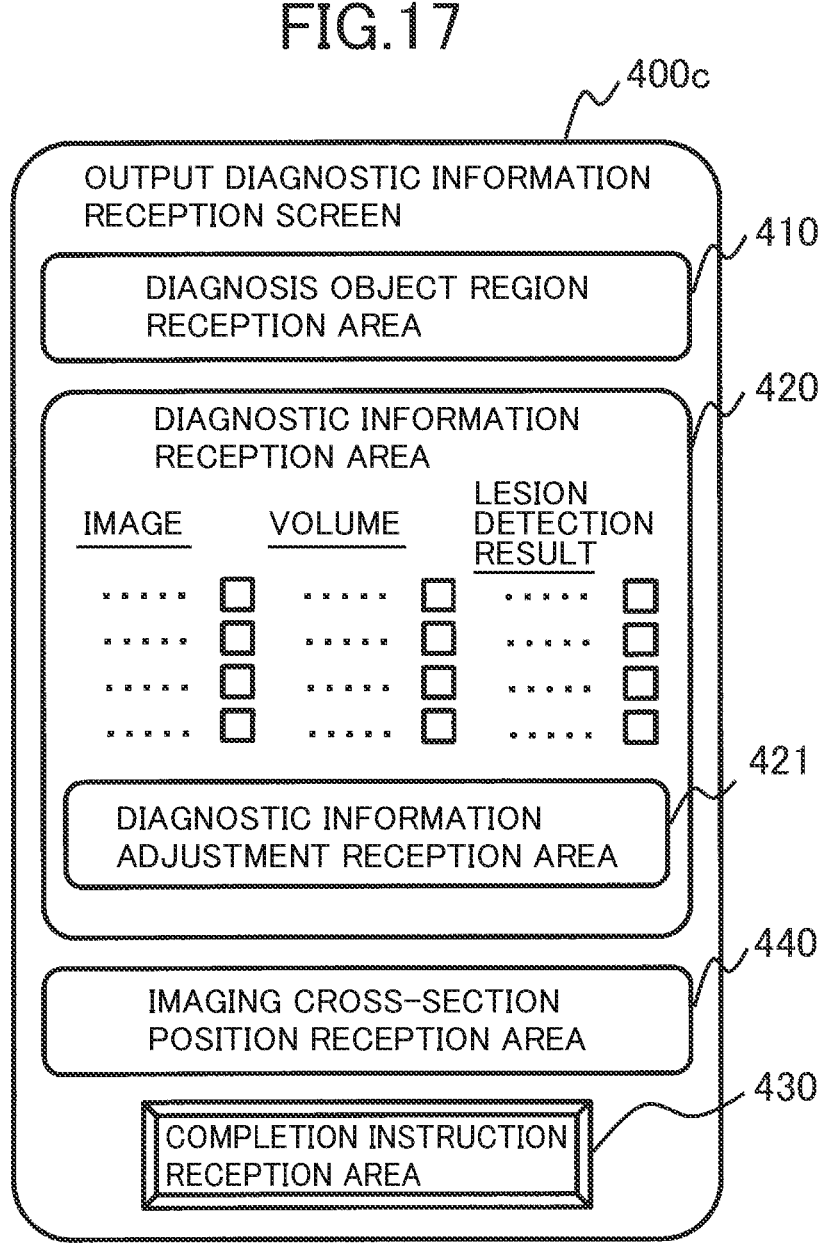

MEDICAL IMAGE PROCESSING AND DIAGNOSTIC IMAGE GENERATION DEVICE FOR PREDETERMINED TYPES OF DIAGNOSTIC INFORMATION

TECHNICAL FIELD

The present invention relates to a medical diagnostic imaging support technique using measurement data obtained by means of a medical image acquisition apparatus.

BACKGROUND ART

There have been known medical image acquisition apparatuses, such as Magnetic Resonance Imaging (hereinafter, referred to as MRI) apparatuses, CT (Computed Tomography) apparatuses, and ultrasonic diagnostic equipment which are adapted for non-invasive acquisition of anatomic tomographic images of human body. According to these apparatuses, an image obtained by computing acquired measurement data is displayed as a diagnostic image on a display unit associated with the apparatus or on a display unit independent from the apparatus.

An image using a physical property value of living tissue (e.g., T1: longitudinal relaxation time, T2: transverse relaxation time, PD: proton density, D: diffusion coefficient, CT value and the like) as a pixel value is useful in diagnosis of various diseases such as early diagnosis for knee osteoarthritis. Further, such an image is unsusceptible to device parameters derived from hardware and hence, is also useful for clinical researches performed at plural centers.

In the MRI apparatus, for example, RF pulses and gradient magnetic field pulses are applied based on predetermined pulse sequence and imaging parameter, so as to acquire echo signals, based on which an image is formed. At this time, a user can obtain an emphasized image emphasizing relative difference in the physical property of living tissue (e.g., T1: longitudinal relaxation time, T2: transverse relaxation time, PD: proton density, D: diffusion coefficient, and the like) by selecting a pulse sequence. To change the degree of emphasis or the physical property value of an object, the user needs to select another pulse sequence or change the imaging parameter.

It takes much time for the MRI apparatus to make quantitative measurement of the physical property of living tissue. In clinical tests, therefore, an emphasized image generated based on an imaging sequence is commonly used as a diagnostic image. In the diagnosis using such an emphasized image, the diagnosis is made by comparing the signal levels of different types of images. This leads to an increase in the image types and thence, in information volume, which makes diagnosis work cumbersome and complicated. In the case of the MRI apparatus, the emphasized image generated based on the imaging sequence is limited in emphasis pattern. According to a sequence for acquiring a blood vessel image, for example, fat tissue images as well as blood vessel images are simultaneously acquired at high signal levels. This results in post processing involving a clipping operation and the like for removing the fat tissues, which requires much time and an effort of the user.

More recently, on the other hand, there have been proposed a method for high-speed measurement of T1 value or T2 value by using SSFP (Steady State Free Precision) which is a GrE sequence (see, for example, Non-patent Literature 1), and a method of estimating a physical property value as a test subject parameter from a function determined by a numerical simulation (see, for example, Patent Literature 1).

CITATION LIST

Non-Patent Literature

Non-patent Literature 1: Deoni SC "Transverse relaxation time (T2) mapping in the brain with off-resonance correction using phase-cycled steady-state free precession imaging" J Magn Reson Imaging 2009, 30, p 411-417

Patent Literature

Patent Literature 1: Japanese Unexamined Patent Application Publication No. 2011-24926

SUMMARY OF INVENTION

Technical Problem

As described in Non-patent Literature 1, when the physical property value of tissue is determined by means of the MRI apparatus, a quantitative value image indicating the physical property value can be usable as a diagnostic image. Further, in a case where a function of signal intensity is theoretically obtainable, an emphasized image can be formed using an arbitrary imaging parameter. Therefore, making measurement of the physical property value provides an increase in the number of types of imageable images.

In a case where the quantitative value image is used as the diagnostic image, the improvement in diagnostic accuracy is expected because of the increased diagnostic information in conjunction with the increased types of imageable images. However, the diagnosis work becomes cumbersome and complicated because of the need for comparing plural types of images.

In view of the above problem, the present invention has been accomplished and the object thereof is to provide a technique for supporting the diagnosis by reducing the user's time and effort in quantitative diagnosis using the quantitative value acquired by the medical image acquisition apparatus.

Solution to Problem

According to an aspect of the present invention, the user is allowed in advance to select only a desired type of diagnostic information from vast amounts of diagnostic information such as images and numerical values. Only the selected type of diagnostic information is presented to the user in a user-friendly mode. The diagnostic information is calculated by using a physical property value necessary for the calculation of the diagnostic information in question and calculation information such as arithmetic functions and variables, the physical property value and calculation information being stored in advance.

Specifically, the present invention provides a medical diagnostic imaging support apparatus including: an output diagnostic information reception portion for receiving a type of outputted diagnostic information as output diagnostic information; a physical property value calculation portion for calculating a physical property value from measurement data acquired by a medical image acquisition apparatus; a diagnostic information calculation portion for calculating the output diagnostic information by using the physical property value; and a display processor for generating a display screen from the calculated output diagnostic information and displaying the display screen.

The present invention further provides a medical diagnostic imaging support method including: an output diagnostic information reception step of receiving the designation of a type of outputted diagnostic information; a physical property value calculation step of calculating a physical property value from an echo signal acquired by a magnetic resonance imaging apparatus; a diagnostic information calculation step of calculating the type of diagnostic information, as received at the output diagnostic information reception step, by using the physical property value; and a display processing step of generating display screen data from the calculated output diagnostic information and displaying the display screen data.

Advantageous Effects of Invention

The present invention can reduce time and an effort expended by the user or a diagnostician in the quantitative diagnosis.

BRIEF DESCRIPTION OF DRAWINGS

FIG. 3 is a flow chart showing the steps of a diagnostic information calculation process according to the first embodiment hereof.

FIG. 4 is an explanatory chart showing information items stored in an information storage portion according to the first embodiment hereof.

FIG. 5 is an explanatory diagram showing an exemplary output diagnostic information reception screen according to the first embodiment hereof.

FIG. 14 is an explanatory chart showing information items stored in an information storage portion according to the third embodiment hereof.

FIG. 17 is an explanatory diagram showing an exemplary output diagnostic information reception screen according to the modification of the embodiment hereof.

DESCRIPTION OF EMBODIMENTS

<<First Embodiment>>

Figure 1:
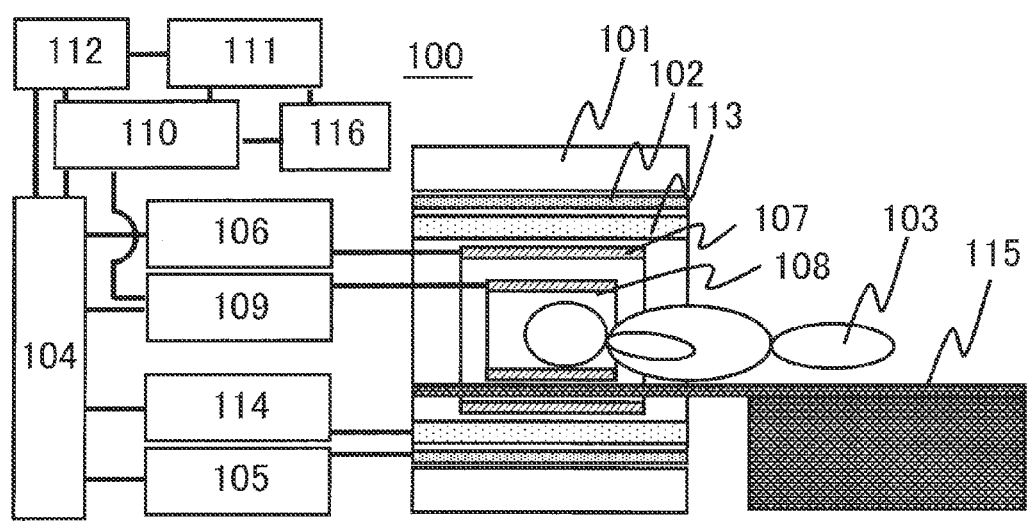
FIG. 1 is a block diagram showing a typical configuration of an MRI apparatus according to a first embodiment of the present invention.

A first embodiment to which the present invention is applied is described as below. Unless otherwise specifically noted, the same or similar reference numerals in the drawings illustrating the embodiments hereof are used to refer to the same or similar components which are explained only once to avoid repetition.

The embodiment of the present invention is described as below by way of an exemplary case where a magnetic resonance imaging (MRI) apparatus is used as the medical image acquisition apparatus while a medical diagnostic imaging support apparatus is incorporated in the MRI apparatus for medical image acquisition.

First, description is made on the magnetic resonance imaging (MRI) apparatus including the medical diagnostic imaging support apparatus according to the embodiment.

The MRI apparatus is a medical diagnostic imaging apparatus principally utilizing proton nuclear magnetic resonance phenomenon. The MRI apparatus is capable of non-invasive imaging of any cross-section and acquisition of not only morphologic information but also information on vital functions such as blood flow and metabolic function. In general, the apparatus excites nuclear magnetization in a cross-section to be imaged by applying a slice gradient magnetic field to a test subject placed in a magnetostatic field and simultaneously applying thereto a high-frequency magnetic field (RF) pulse of a particular frequency. Plan position information is imparted to the excited nuclear magnetization by applying a phase encode gradient magnetic field and a readout gradient magnetic field, so as to measure NMR signal (echo signal) generated by nuclear magnetization. The measurement of the NMR signal is repeated till a measurement space called a "k-space" is filled with the signals. The signals filled in the k-space are visualized through inverse Fourier transform.

The RF pulse and the gradient magnetic fields for generating the echo signal are each applied according to a predetermined pulse sequence and imaging parameter. This pulse sequence is known to include a variety of types for any purposes. For example, a high-speed imaging method of gradient echo type (GrE) is a method in which a required number of NMR signals for acquiring one cross-sectional image are measured by sequentially changing a phase encode gradient magnetic field for each repetition time (hereinafter, referred to as "TR") of the pulse sequence.

The imaging parameters are for controlling the individual pulses applied based on the pulse sequence and the individual gradient magnetic fields, and include: repetition time TR, echo time TE, flip angle α deciding the intensity of RF pulse, coordinate phase θ and the like.

In general MRI scan, an imaging region to be diagnosed based on an image acquired by imaging for positioning is set, and plural types of images (e.g., T1-weighted image, T2-weighted image, FLAIR, diffusion weighted image, and MRA) are acquired by changing the pulse sequence or the imaging parameter. The user generates a diagnostic image by manually adjusting the window level (WL) and the window width (WW) of the acquired image and clipping signals becoming hindrance to diagnosis on an as-needed basis.

As described above, an MRI apparatus 100 according to the embodiment excites the nuclear magnetization in a test subject 103 by applying the high-frequency magnetic field to the test subject 103 in placed the magnetostatic field, and makes measurement of a generated nuclear magnetic resonance signal (NMR signal, echo signal). At this time, the position information is imparted to the measured magnetic resonance signal by applying the gradient magnetic field, so as to visualize (photograph) the magnetic resonance signal.

FIG. 1 is a block diagram showing a typical configuration of the MRI apparatus 100 according to this embodiment implementing the present invention. The MRI apparatus 100 of this embodiment includes: a magnet 101 generating the magnetostatic field; a gradient magnetic field coil 102 generating the gradient magnetic field; an RF coil 107 for applying a high-frequency magnetic field pulse (hereinafter, referred to as "RF pulse") to the test subject (living body) 103; an RF probe 108 for detecting the echo signal emitted from the test subject 103; and a table 115 carrying thereon the test subject (e.g., live body) 103 in a magnetostatic field space generated by the magnet 101.

The MRI apparatus 100 of this embodiment further includes: a gradient magnetic field power supply 105 for driving the gradient magnetic field coil 102; a high-frequency magnetic field generator 106 for driving the RF coil 107; a receiver 109 for receiving the echo signal detected by the RF probe 108; a sequencer 104 which sends a command to the gradient magnetic field power supply 105 and the high-frequency magnetic field generator 106 to drive them to generate the gradient magnetic field and the high-frequency magnetic field, respectively, and which sets a nuclear magnetic resonance frequency, as a detection reference, in the receiver 109; a computing machine 110 for performing signal processing on the detected signal; a display unit 111 for displaying the result of processing executed by the computing machine 110; a storage unit 112 for storing the processing result; and an input device 116 for receiving an instruction from the user. The storage unit 112 further stores a variety of data items required for the processing performed by the computing machine 110.

The MRI apparatus 100 may further include a shim coil 113, and a shim power supply 114 for driving the shim coil 113 if it is necessary to adjust the magnetostatic field homogeneity. The shim coil 113 includes a plurality of channels, and operates on current supplied from the shim power supply 114 so as to generate an additional magnetic field for correction of a nonhomogeneous magnetostatic field. During the adjustment of the magnetostatic field homogeneity, the electric current supplied to the respective channels of the shim coil 113 is controlled by the sequencer 104.

In the MRI apparatus 100 having the above configuration, the sequencer 104 provides control such that the RF pulse is applied to the test subject 103 by means of the RF coil 107 while a gradient magnetic field pulse for supplying the position information, such as slice selection and phase encode, to the echo signal is applied by the gradient magnetic field coil 102. The signal emitted from the test subject 103 is received by the RF probe 108. The detected signal is sent to the computing machine 110 where the signal is processed for image reconstruction and the like. The storage unit 112 may be adapted to store not only the signal processing results but also the detected signal per se, imaging conditions and the like on an as-needed basis.

The computing machine 110 is responsible not only for processing the received signal but also for controlling the operations of the whole MRI apparatus 100. For example, the computing machine outputs instructions to the sequencer 104 so as to operate the individual components at a preprogrammed timing or intensity, thus controlling the operations of the components of the MRI apparatus 100 and taking measurements. The pulse sequences describe, in particular, the timings and the intensities of the high-frequency magnetic field, gradient magnetic field, and signal reception, out of the above programs. As described above, the measurement is performed according to the pulse sequence and the imaging parameters required for controlling the measurement. The pulse sequence is generated in advance and stored in the storage unit 112, while the imaging parameter is inputted by the user via a user interface.

The MRI apparatus 100 is capable of imaging any imaging cross-section of a test subject to be imaged by controlling the timings and intensities of the high-frequency magnetic field and the gradient magnetic field, which are set in the pulse sequences. A desired imaging cross-section is commonly imaged by deciding the position of the imaging cross-section relative to the test subject to be imaged and reflecting the decided position in the pulse sequence.

The computing machine 110 also performs user interface processing of controlling the user interfaces for the input device 116, the display unit 111 and the like, presenting the processing results to the user, and receiving input from the user. Further, the computing machine processes the echo signal acquired by the MRI apparatus 100, reconstructing an image. Otherwise, the computing machine processes the echo signal to calculate a control value required for imaging, such as center frequency or RF irradiation intensity, and transmits the calculation result to the sequencer 104.

Further, the computing machine 111 of this embodiment calculates a user-selected type of diagnostic information from the echo signal acquired by the MRI apparatus 100 and displays the resultant diagnostic information by way of the display unit 111.

Figure 2:
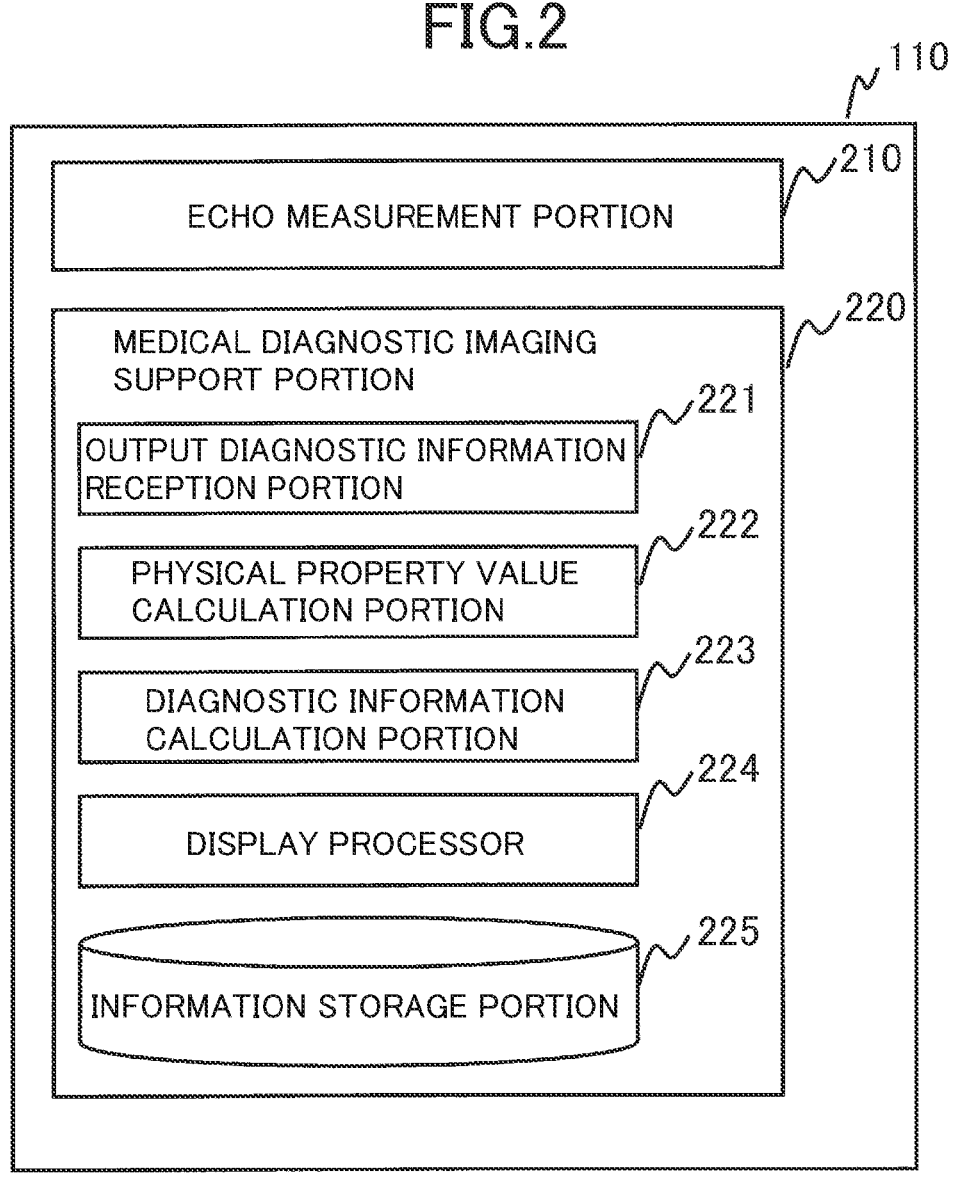
FIG. 2 is a functional block diagram of a computing machine according to the first embodiment hereof.

As shown in FIG. 2, the computing machine 110 of the embodiment includes for implementation of this function: an echo measurement portion 210 which controls the individual components according to a predetermined pulse sequence so as to apply the high-frequency magnetic field and the gradient magnetic field to the test subject 103 placed in the magnetostatic field and to acquire the echo signal emitted from the test subject 103; and a medical diagnostic imaging support portion 220 which gives a presentation to the user by generating desired diagnostic information from the acquired echo signal and outputting the resultant information.

The medical diagnostic imaging support portion 220 of the embodiment includes: an output diagnostic information reception portion 221 which receives a type of diagnostic information to be outputted as an output diagnostic information item; a physical property value calculation portion 222 which calculates a physical property value from the measurement data (the echo signal) acquired by the medical image acquisition apparatus; a diagnostic information calculation portion 223 which calculates the output diagnostic information by using the physical property value; a display processor 224 which generates a display screen from the calculated diagnostic information and displays the resultant display screen at the display unit 111; and an information storage portion 225 which stores functions, variables and the like which are required for the calculation of the diagnostic information.

The computing machine 110 of the embodiment includes a CPU and a memory. The functions of the computing machine 110 are each implemented by the CPU loading software (program) stored in advance in the storage unit 112 into the memory thereof and executing the software. The information storage portion 225 is constructed on the storage unit 112. It is noted that all of the above functions do not need to be implemented in the software but some or all of the functions may be implemented by hardware such as ASIC (Application Specific Integrated Circuit).

The types of diagnostic information specified by the user as the output diagnostic information include at least one of image based on the physical property value of living tissue; volume of a predetermined area; existence probability of the area in question; detection result of lesion (lesion detection result); and disease name.

The images based on the physical property value of the living tissue include, for example: emphasized image emphasizing a parameter (test subject parameter) depending upon a predetermined test subject, such as T1-weighted image, T2-weighted image, diffusion weighted image, and FLAIR; physical property value image about T1 value, T2 value, PD (proton density), magnetic susceptibility, diffusion coefficient, diffusion anisotropy, diffusion kurtosis, axon diameter, conductivity and the like; segment image of each segmented anatomic component such as gray matter and white matter; image of extracted abnormal tissue sustaining calcification, edema, inflammation, tumor, bleeding and the like; structure image such as of blood vessel and the like. The image may further include an image of an emphasized pattern that is unobtainable with a normal pulse sequence.

The area for determination of volume or existence probability includes, for example, the anatomic component such as gray matter and white matter, and the abnormal tissues sustaining calcification, edema, inflammation, tumor, bleeding or the like. The lesion to be detected includes neoplastic lesion, lesion suspected of being associated with hydrencephalus, lacunar infarct, multiple sclerosis or the like.

A flow of calculation process of the diagnostic information by the individual portions of the computing machine 110 of the embodiment is described as below. FIG. 3 is a flow chart showing the steps of a diagnostic information calculation process according to the embodiment.

First, the user selects a desired type of diagnostic information via the interface. The output diagnostic information reception portion 221 receives the user-specified type of diagnostic information as the output diagnostic information (Step S1101). The output diagnostic information is stored in the information storage portion 225.

Next, in response to an imaging instruction from the user, the echo measurement portion 210 acquires an echo signal by controlling the pulse sequence (Step S1102).

The physical property value calculation portion 222 calculates a physical property value from the acquired echo signal (Step S1103).

Next, the diagnostic information calculation portion 223 refers to the information storage portion 225 and calculates the output diagnostic information selected in Step S1101 by using the physical property value (Step S1104).

Finally, the display processor 224 displays the calculated output diagnostic information at the display unit 111 (Step S1105).

Step S1101 and Step S1102 can replace each other. In a case where Step S1102 precedes Step S1101, the acquired echo signal is stored in the storage unit 112. After the output diagnostic information is selected, the operations from Step S1103 onward are performed. The flow where the acquisition of the echo signal is followed by the selection of the output diagnostic information permits the acquisition of an additional desired diagnostic information piece even where another diagnostic information piece becomes necessary after image acquisition.

[Information Storage Portion]

The information storage portion 225 stores: data on receivable (selectable) regions which an output information reception portion 211 can receive, and data for use in calculation of the diagnostic information. The data used for the calculation of the diagnostic information includes the physical property value (input physical property value) required for the calculation of the diagnostic information in question, and calculation information used for the calculation of the diagnostic information in question. The calculation information includes functions and variables.

The information storage portion 225 of the embodiment stores calculable diagnostic information on a per-region basis. As shown in FIG. 4, the information storage portion further stores, for each type of diagnostic information, the types of physical property values (input physical property value) 302, and functions and variables (calculation information) 303 used for the calculation of the diagnostic information in question. The input physical property value 302 and the calculation information 303 are stored in correspondence to information for identification of the type of diagnostic information (hereinafter, referred to as "diagnostic information name 301").

The details of each function are described as below.

[Output Diagnostic Information Reception Portion]

The output diagnostic information reception portion 221 generates a user interface screen (output diagnostic information reception screen) for receiving the type of diagnostic information and displays the resultant screen by way of the display unit 111. The output diagnostic information reception portion 221 receives specified output diagnostic information via the output diagnostic information reception screen in question. The user manipulates the input device 116 to enter the type of diagnostic information.

FIG. 5 shows an exemplary output diagnostic information reception screen 400 for receiving the selection of output diagnostic information. According to the embodiment, the MRI apparatus receives a diagnosis object region and the output diagnostic information via the output diagnostic information reception screen 400. Therefore, the output diagnostic information reception screen 400 of the embodiment includes: a diagnosis object region reception area 410 for receiving a diagnosis object region; a diagnostic information reception area 420 for receiving the specified output diagnostic information; and a completion instruction reception area 430 for receiving an input completion instruction.

The diagnosis object region reception area 410 may be configured, for example, to display a list of selectable diagnosis object regions, any one of which the user can select. The selectable diagnosis object regions include, for example: brain, liver, heart, spine, lower limb, knee and the like. The listed diagnosis object regions are extracted from the information storage portion 225.

The diagnostic information reception area 420 displays a list of the above-described diagnostic information names as the diagnostic information that can be outputted, anyone of which the user can select. The listed diagnostic information names are extracted from the information storage portion 225. The types of diagnostic information are listed in a menu-driven system with check boxes, any of which the user can check. As shown in FIG. 5, for example, the diagnostic information types such as image, volume and lesion detection result may be displayed on a per-category basis.

When the user gives a selection completion instruction via the completion instruction reception area 430, the output diagnostic information reception portion 221 responds to the instruction by storing the presently selected diagnosis object region and output diagnostic information in the storage unit 112.

[Physical Property Value Calculation Portion]

Arithmetic processing performed by the physical property value calculation portion 222 of the embodiment is described in detail. The physical property value calculation portion 222 of the embodiment first generates a signal function for a predetermined imaging sequence, and calculates the physical property value using the resultant signal function. According to this embodiment, the physical property value is obtained by fitting a plurality of echo signals measured in the imaging sequence to the signal function, followed by estimating the physical property value as a variable of the signal function. The generated signal function and the calculated physical property value are stored in the storage unit 112.

The following description is made by way of an example where RF-spoiled Grass sequence is used as the predetermined imaging sequence.

The physical property value calculation portion 222 first performs a numerical simulation to generate a signal function fs. The signal function fs is a function generated for each imaging sequence. The signal function includes, as variables, at least one of a parameter (test subject parameter) dependent on the test subject representing the physical property value of living tissue and a parameter (apparatus parameter) dependent on the apparatus, and an imaging condition (imaging parameter) defined by the user when performing the pulse sequence. The function returns a signal intensity of each pixel.

Changeable imaging parameters in the RF-spoiled Grass sequence are flip angle (FA), repetition time (TR), echo time (TE) and phase incremental of RF ($\theta$). Of these, the parameter $\theta$ is normally fixed to 117° such that an image contrast having as little T2-dependence as that of FLASH can be obtained. FLASH is one of the high-speed imaging methods. When this parameter $\theta$ is varied, the image contrast is significantly varied in the T2-dependence.

The test subject parameters include the longitudinal relaxation time (T1), the transverse relaxation time (T2), chemical shift (Cs), and proton density (PD). The apparatus parameters include magnetic field intensity (B0), irradiation intensity (B1) of transmission coil, and sensitivity (Sc) of reception coil.

The function fs of the RF-spoiled Grass signal is expressed by the following equation (1) using the above parameters.

[Equation 1]

$$I = fs(T1, T2, Cs, PD, B1 \times FA, TR, TE, \theta, B0, Sc) \quad (1)$$

The signal function fs is generated by numerical simulation exhaustively varying the imaging parameter against an arbitrary value of each of the test subject parameters T1, T2, Cs, followed by interpolation. It is provided here that PD, B1 and Sc of an imaging object are a fixed value (e.g., 1).

Further, B0 is defined to be the same as the magnetic field intensity of an apparatus used for imaging (e.g., 3T).

The numerical simulation employs a test subject model with spins on grid points, and the imaging sequence, imaging parameter and apparatus parameter as inputs. The numerical simulation outputs the NMR signal by solving Bloch equation which is a basis equation describing magnetic resonance phenomenon.

The test subject model is given as special distribution of the spin ($\gamma$, M0, T1, T2, Sc), where $\gamma$ denotes a gyromagnetic ratio, and M0 denotes thermal equilibrium magnetization (proton density). Image acquisition under given conditions can be accomplished by reconstructing an image from the NMR signals.

Bloch equation is a first-order linear normal differential equation and expressed by the following equation (2).

[Equation 2]

$$\frac{d}{dt}\begin{pmatrix} Mx \\ My \\ Mz \end{pmatrix} = \begin{pmatrix} -1/T2 & \gamma H & \\ -\gamma H & -1/Y2 & \gamma H1 \\ & -\gamma H1 & -1/T1 \end{pmatrix}\begin{pmatrix} Mx \\ My \\ Mz \end{pmatrix} + \begin{pmatrix} 0 \\ 0 \\ M0/T1 \end{pmatrix} \quad (2)$$

$$H = B0 + G_x x + G_y y + G_z z + 2\pi f0/\gamma G_s B0$$

where (x, y, z) denotes a three-dimensional orthogonal coordinate system, and z represents a direction of magnetostatic field (intensity: B0). (Mx, My, Mz) denotes the spin while $G_x$, $G_y$, $G_z$ each denote the intensity of gradient magnetic field of a direction represented by the subscript. H1 denotes the intensity of high-frequency magnetic field, and f0 denotes the frequency of a rotating coordinate system.

Next, the physical property value calculation portion 222 estimates the test subject parameter and/or the apparatus parameter. In this embodiment, the test subject parameter and/or the apparatus parameter is estimated by the steps of: acquiring a plurality of images by performing the RF-spoiled Grass sequence while varying the imaging parameters FA, TR, TE and $\theta$, and fitting the per-pixel signal value I to fs.

It is noted, however, that it is difficult to freely control the apparatus parameter during the execution of the imaging sequence. Further, the imaging parameters except for B1 cannot be separated by merely varying the imaging parameters. Therefore, the signal function fs is fitted to a function f whose variables are transformed as expressed by the following equation (3).

[Equation 3]

$$I = fs(T1, T2, Cs, PD, B1 \times FA, TR, TE, \theta, B0, Sc) \quad (3)$$
$$= f(T1, T2, \Delta f0, a, B1 \times FA, TR, TE, \theta)$$
$$a = PD \times Sc$$
$$\Delta f0 = Cs \times B0$$

The physical property value calculation portion 222 uses the above-described method for estimating the test subject parameters T1 and T2; the apparatus parameter B1; and $\Delta f0$ and 'a' which are the products of the test subject parameter and the apparatus parameter. A least-square method is applicable to the function fitting. The physical property value is calculated by estimating the physical property as a test subject parameter.

It is noted that the calculation method of the physical property value is not limited to this. For example, the following steps may be taken: repeating an imaging operation while varying the imaging parameter in a pulse sequence with formulated signal intensity, and determining the physical property value by using a signal intensity function formulated from the signal intensity of the acquired images.

[Diagnostic Information Calculation Portion]

The diagnostic information calculation portion 223 uses the physical property value determined by the physical property value calculation portion 222 so as to calculate diagnostic information of a type selected as the output diagnostic information. For calculation, the diagnostic information calculation portion uses the function and variable for calculation of the diagnostic information, which are stored in the information storage portion 225. Specifically, the diagnostic information calculation portion 223 calculates the output diagnostic information by using the input physical property value 302, out of the physical property values calculated by the physical property value calculation portion 222, and the calculation information 303, the input physical property value 302 and the calculation information 303 stored in the information storage portion 225 in correspondence to the output diagnostic information. In a case where plural types of diagnostic information items are selected as the output diagnostic information, all the output diagnostic information items are calculated.

It is assumed, for example, that T1, T2, PD as the input physical property values 302; TR=0.5, TE=0.013 as the variables of the calculation information 303; and the following equation (4) as the function are stored in the information storage portion 225 in correspondence to "T1-weighted image" of the diagnostic information name 301.

[Equation 4]
$$S(T1, T2, PD) = PD\left(1 - \text{Exp}\left[-\frac{TR}{T1}\right]\right) \text{Exp}\left[-\frac{TE}{T2}\right] \quad (4)$$

In the case where the T1-weighted image is selected as the output diagnostic information, the diagnostic information calculation portion 223 calculates a signal intensity S of each voxel by substituting the above input physical property values 302 calculated by the physical property value calculation portion 222 and the variables of the above calculation information 303 in the equation (4).

Further, it is assumed that T1, T2 as the input physical property values 302; tc1=0.55, tc2=0.06, θ=π/36, w1=0.02, w2=0.01, σ1=0.1, 62=0.02 as the variables of the calculation information 303; and the following set of equations (5) to (7) as the functions are stored in the information storage portion 225 in correspondence to "white matter existence probability map" of the diagnostic information name 301.

[Equation 5]
$$\begin{pmatrix} p \\ q \end{pmatrix} = \begin{pmatrix} \cos[-\theta] & -\sin[-\theta] \\ \sin[-\theta] & \cos[-\theta] \end{pmatrix} \begin{pmatrix} T1 - tc1 \\ T2 - tc2 \end{pmatrix} \quad (5)$$

$$f(x, w, \sigma) = \begin{cases} \text{Exp}\left[-\frac{x^2}{2\sigma^2}\right] & (|x| > w) \\ 1 & (|x| \leq w) \end{cases} \quad (6)$$

$$P(p, q, w1, w2, \sigma1, \sigma2) = f(p, w1, \sigma1)f(q, w1, \sigma2) \quad (7)$$

In the case where the white matter existence probability map is selected as the output diagnostic information, the diagnostic information calculation portion 223 calculates an existence probability P by substituting the above input physical property values 302 calculated by the physical property value calculation portion 222 and the variables of the above calculation information 303 in the set of equations (5) to (7).

Further, it is assumed that T1, T2 as the input physical property values 302; tc1=0.9, tc2=0.9, θ=0, w1=0.0, w2=0.0, σ1=1.0, σ2=0.3 as the variables of the calculation information 303; and the above set of equations (5) to (7) as the functions are stored in the information storage portion 225 in correspondence to "edema image" of the diagnostic information name 301.

In the case where the edema image is selected as the output diagnostic information, the diagnostic information calculation portion 223 calculates P by substituting the above input physical property values 302 calculated by the physical property value calculation portion 222 and the variables of the above calculation information 303 in the above set of equations (5) to (7). The P is defined as the signal intensity of each pixel.

Further, it is assumed that T1, T2 and voxel size v as the input physical property values 302; tc1=0.9, tc2=0.9, θ=0, w1=0.0, w2=0.0, σ1=1.0, σ2=0.3 as the variables of the calculation information 303; and the above set of equations (5) to (7) as the functions are stored in the information storage portion 225 in correspondence to "white matter volume" of the diagnostic information name 301.

In the case where the white matter volume is selected as the output diagnostic information, the diagnostic information calculation portion 223 calculates an existence probability of white matter P by substituting the above input physical property values 302 calculated by the physical property value calculation portion 222 and the above variables of the calculation information 303 in the above set of equations (5) to (7). Subsequently, the diagnostic information calculation portion determines the white matter volume by integrating the volume v of each voxel over the existence probability P in question.

[Display Processor]

As described above, the display processor 224 generates display screen data (hereinafter, simply referred to as "display screen") from the calculated output diagnostic information and presents the resultant display screen by way of the display unit 111. As described above, the diagnostic information calculated by the diagnostic information calculation portion 223 using each of the above equations is not limited to the output diagnostic information. The display processor 224 extracts only a user-selected output diagnostic information item from among the various diagnostic information items so calculated, generates a display screen from the extracted information and displays the display screen by way of the display unit 111. However, in a case where plural types of diagnostic information items are selected, all the selected types of diagnostic information items are incorporated into the display screen and displayed at the display unit 111.

As described above, the types of diagnostic information include image, volume, existence probability, lesion detection result, disease name (diagnostic information type) and the like. The following description is made by way of example where the types of diagnostic information (diagnostic information type) include at least one of image, volume and lesion detection result.

Figure 6:
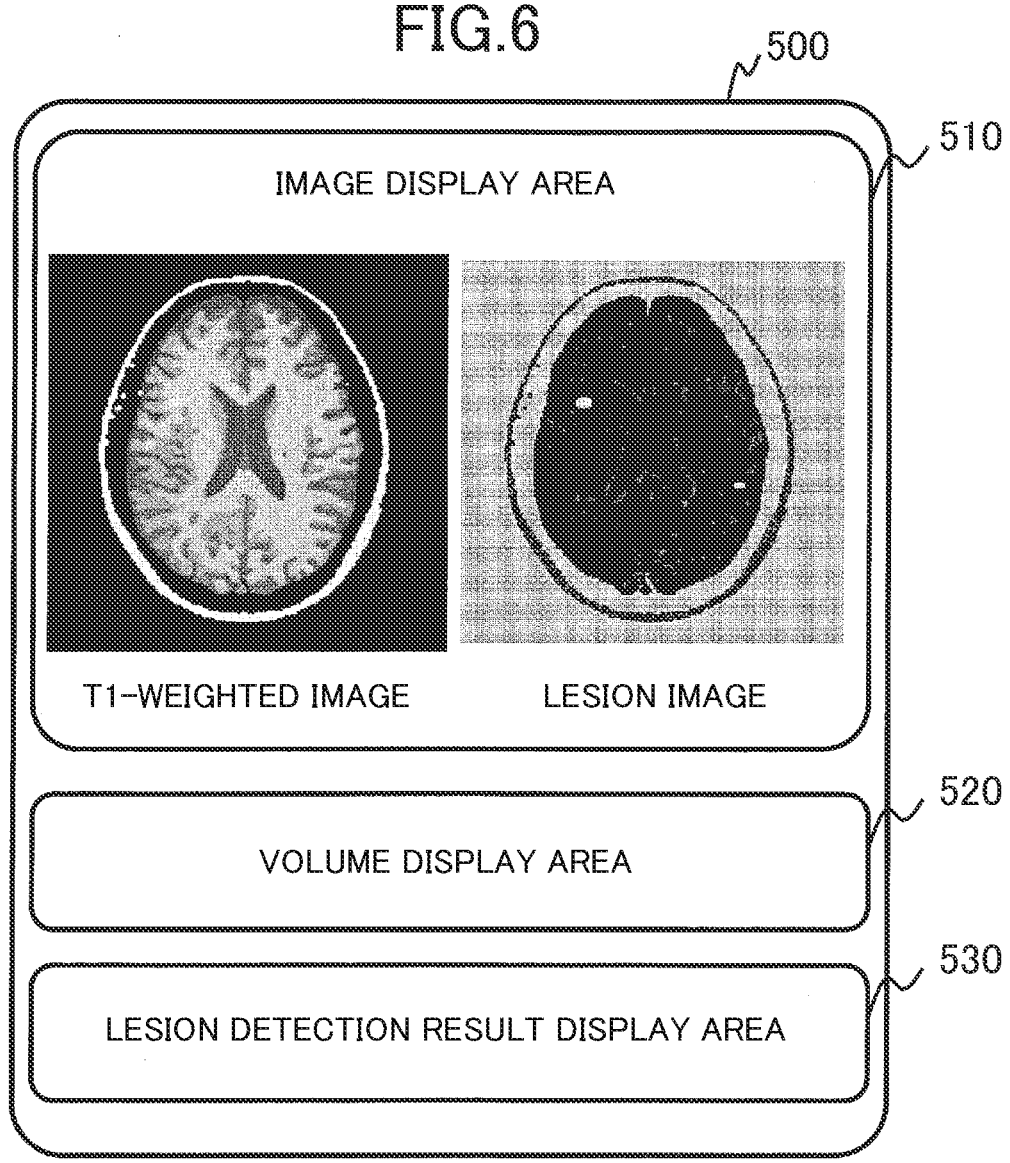
FIG. 6 is an explanatory chart showing an exemplary display screen according to the first embodiment hereof.

FIG. 6 shows an example of a display screen 500 generated by the display processor 224. As shown in the figure, the display screen 500 includes a display area per diagnostic information type. Specifically, the display screen 500 includes: an image display area 510 for displaying an image; a volume display area 520 for displaying a calculated volume; and a lesion detection result display area 530 for displaying a lesion detection result. These areas are generated in accordance with a user-selected output diagnostic information item.

The lesion detection results may be displayed as follows, for example. After the calculation of the existence probability P of respective lesions, the respective volumes of the lesions are calculated, and the lesion detection results are listed in the descending order of volume.

Further, the display processor 224 may generate an image (lesion region image) as the lesion detection result and display the resultant image at the image display area 510. In the lesion region image, the lesion region may be superimposed on an image, such as a segmentation image, that shows the structure of an area including the lesion region in question. At this time, the image display area may be configured to display the lesion regions in different colors, respectively. Showing the lesion region superimposed on the structure image permits a diagnostician to easily understand a positional relation of the lesion.

Further, the display processor 224 may also display an abnormality image (extraction image of abnormal tissue) in a manner to make the difference in the characteristics of the lesion more recognizable. For example, different characteristics of lesions (tumor, fibrosis, calcification, bleeding and edema) are shown in different colors, respectively. The display processor is also adapted to calculate respective existence probabilities of bleeding area, dry tumor and edema, and to generate an image representing the calculated values in color intensities of red, green and blue of the RGB color system, respectively. This facilitates the comprehension of the characteristic of the lesion without comparing a plurality of images, leading to an enhanced diagnostic efficiency.

As described above, the MRI apparatus 100 of this embodiment includes: the echo measurement portion 210 which measures an echo signal emitted from a test subject by applying the high-frequency magnetic field and the gradient magnetic field to the test subject in the magnetostatic field according to the predetermined imaging condition and the predetermined pulse sequence; and the medical diagnostic imaging support portion 220 which generates desired diagnostic information from the echo signal and outputs the diagnostic information as presentation to the user. The medical diagnostic imaging support portion 220 includes: the output diagnostic information reception portion 221 for receiving a type of the outputted diagnostic information as the output diagnostic information; the physical property value calculation portion 222 for calculating the physical property value from the echo signal; the diagnostic information calculation portion 223 for calculating the output diagnostic information by using the physical property value; and the display processor 224 for generating the display screen from the calculated diagnostic information and displaying the display screen.

The MRI apparatus 100 of this embodiment further includes the information storage portion 225 which stores, for each diagnostic information type, the type of the physical property value as the input physical property value and the function and variable as the calculation information, which are used for the calculation of the diagnostic information in question. The diagnostic information calculation portion 223 calculates the output diagnostic information by using, out of the physical property values calculated by the physical property value calculation portion 222, the input physical property value stored in the information storage portion 225 in correspondence to the output diagnostic information, and the calculation information stored in the information storage portion 225 in correspondence to the output diagnostic information.

The output diagnostic information reception portion 221 receives the output diagnostic information via the output diagnostic information reception screen 400. The output diagnostic information reception screen 400 includes the diagnostic information reception area 420 for receiving the specified output diagnostic information.

According to the embodiment, as described above, the desired diagnostic information can be acquired by using the physical property value calculated in advance. Thus, the embodiment negates the need for executing a plurality of different imaging sequences for acquiring a plurality of specified types of diagnostic information items.

Further, all the user-specified types of diagnostic information items are displayed in a user-friendly manner. The user can view necessary diagnostic information on one screen. Therefore, the user can efficiently view necessary and sufficient information, which results in the improvement in diagnostic efficiency. Particularly, in a case where the medical diagnostic imaging apparatus is the MRI apparatus, a pathological condition can be determined without comparing images acquired by executing a plurality of different imaging sequences.

The types of available diagnostic information also include the quantitative value image using the quantitative value representing the absolute value of a desired physical property value as a pixel value. According to the embodiment, such a quantitative value image can be easily acquired. Thus, the embodiment can easily present to the user an information item indicating, for example, brain shrinkage which is unrecognizable from the emphasized image directly acquired by performing the imaging sequence.

The quantitative value image is a standardized image independent of apparatus, which permits multiple centers to compare images and facilitates multicenter clinical study. Particularly, in a case where the medical image acquisition apparatus is the magnetic resonance imaging apparatus, the apparatus can generate an image of an emphasized pattern which cannot be acquired by using a conventional pulse sequence. Further, the apparatus can also generate an apparatus-independent arbitrary emphasized image suitable for diagnosis. This provides easy comparison of the image with images acquired by other apparatuses, thus facilitating multicenter evaluation of lesions.

As described above, the embodiment can provide the diagnostic information for efficient diagnosis and hence, can support diagnosis using the medical images.

<First Modification>

The output diagnostic information may be made changeable after display. In this case, the output diagnostic information reception portion 221 is configured to receive the output diagnostic information again after the diagnostic information is displayed by the display processor 224. Specifically, the display screen further includes the diagnostic information reception area for receiving specified output diagnostic information. Upon receiving the output diagnostic information via the diagnostic information reception area, the diagnostic information calculation portion 223 calculates the received output diagnostic information by using the physical property value already calculated by the physical property value calculation portion, the signal function, and the calculation information stored in the information storage portion 225. The display processor 224 generates a display screen from the calculated output diagnostic information, and displays the resultant display screen.

Figure 7:
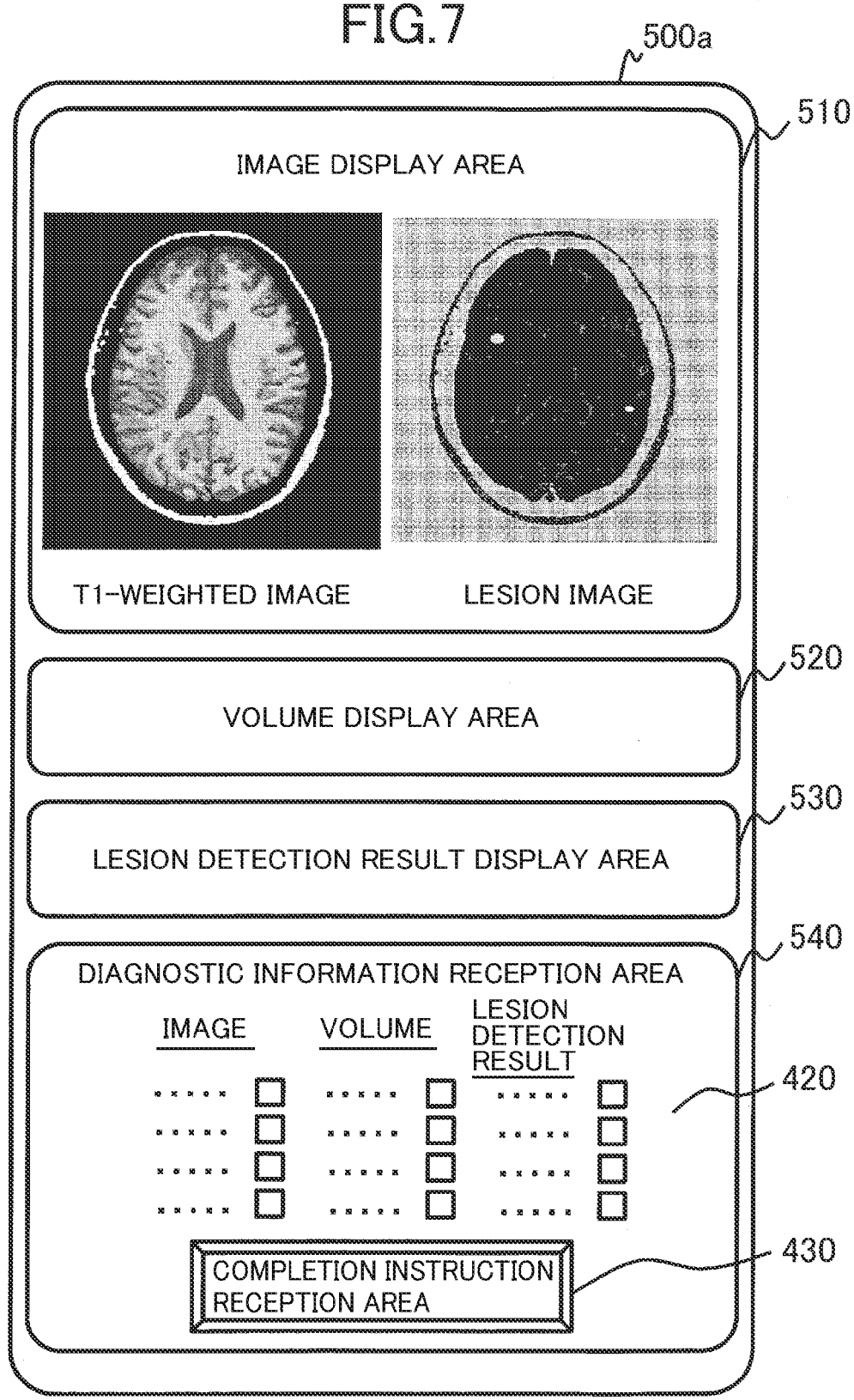
FIG. 7 is an explanatory chart showing an exemplary display screen according to a first modification of the first embodiment hereof.

The display processor 224 generates the diagnostic information reception area in the display screen. FIG. 7 shows an exemplary display screen 500a including the diagnostic information reception area. As shown in the figure, the display screen 500a includes: the image display area 510; the volume display area 520; the lesion detection result display area 530; and a diagnostic information reception area 540.

The diagnostic information reception area 540 has substantially the same configuration as the output diagnostic information reception screen 400 generated by the output diagnostic information reception portion 221. The diagnostic information reception area includes the diagnostic information reception area 420 and the completion instruction reception area 430. However, the diagnostic information reception area does not include the diagnosis object region reception area 410. Namely, the diagnostic information types that are receivable by the diagnostic information reception area 540 are limited to the types of diagnostic information about the diagnosis object region previously received by the diagnosis object region reception area 410 of the display screen 500.

When the user selects new output diagnostic information items via the diagnostic information reception area 540, the output diagnostic information reception portion 221 receives these information items. Then, the output diagnostic information reception portion informs the diagnostic information calculation portion 223 of the output diagnostic information thus received.

The diagnostic information calculation portion 223 calculates the received output diagnostic information by using the signal function and the physical property value stored in the storage unit 112. In this embodiment, the signal function and physical property value necessary for generating the diagnostic information are already generated or calculated, and stored in the information storage portion 225. Further, the input physical property value and calculation information are also stored in the information storage portion 225. Using these value and information, therefore, the diagnostic information calculation portion 223 calculates the new output diagnostic information received via the diagnostic information reception area 540.

Figure 8:
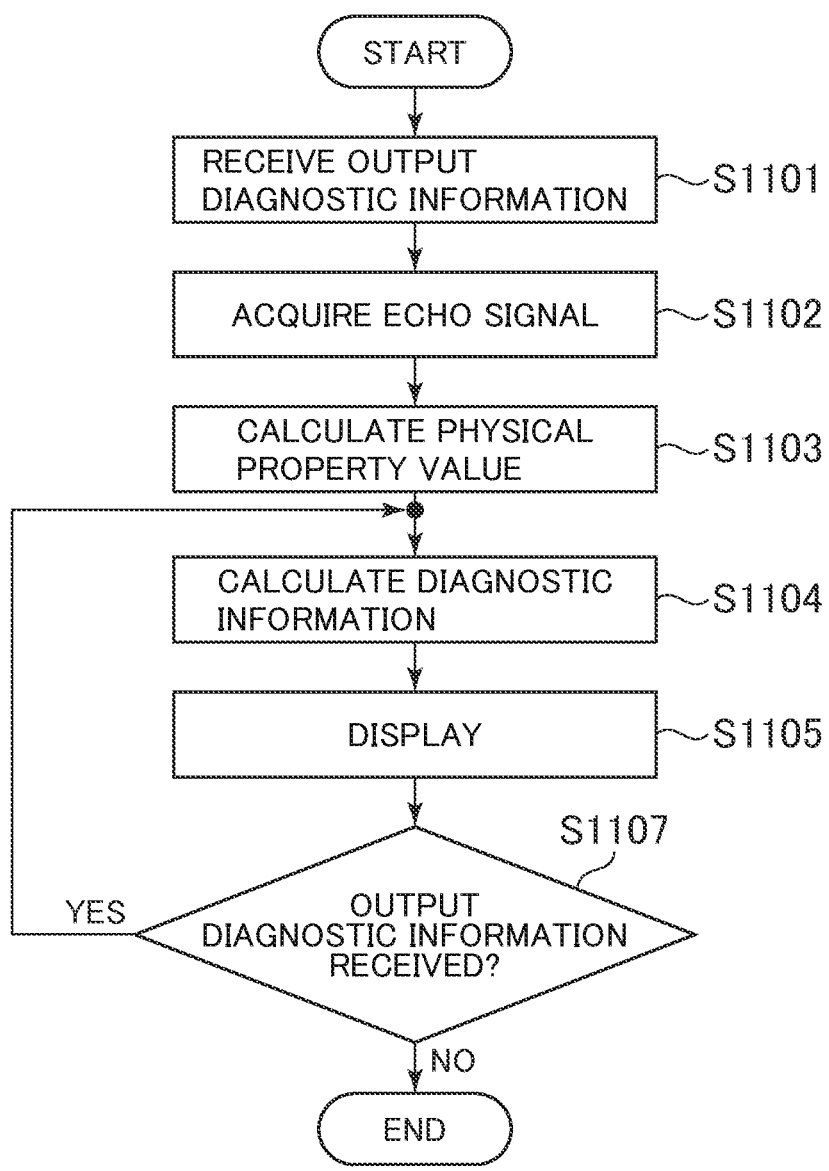
FIG. 8 is a flow chart showing the steps of a diagnostic information calculation process according to the first modification of the first embodiment hereof.

A flow of diagnostic information generation process according to the modification is shown in FIG. 8. The flow to Step S1105 is the same as that of the above embodiment. It is noted, however, that the display screen 500a is shown here. In the subsequent step where the output diagnostic information reception portion 221 receives the new output diagnostic information via the diagnostic information reception area 540 of the display screen 500a, the operation flow returns to Step S1104 to repeat the operations.

In this step, the diagnostic information calculation portion 223 calculates the newly selected output diagnostic information by using the signal function and physical property value stored in the storage unit 112. The display processor 224, in turn, displays the calculation result.

On the other hand, the medical diagnostic imaging support portion 220 terminates the process if no output diagnostic information is specified via the diagnostic information reception area 540.

With the addition of the diagnostic information reception area 540, the display screen 500a is adapted for the change of the diagnostic information to be displayed after the display of the diagnostic information. The diagnostic information calculation portion 223 can calculate the changed output diagnostic information based on the information stored in the information storage portion 225. Such a configuration permits the user to easily acquire a diagnostic information item other than the initially specified type of diagnostic information without performing the imaging operation again. According to this modification, various types of diagnostic information items can be acquired at a desired timing by using the once-calculated physical property value.

<Second Modification>

Further, the apparatus may also be configured to call up and select again a previously set diagnostic information type.

In this case, the output diagnostic information reception portion 221 stores, as an output list, in the information storage portion 225 a set of diagnostic information types defined by the user via the diagnostic information reception area 420 or the diagnostic information reception area 540. Further, in response to an instruction from the user, the output diagnostic information reception portion 221 calls up the output list from the information storage portion 225 so as to permit the selection of information.

Figure 9:
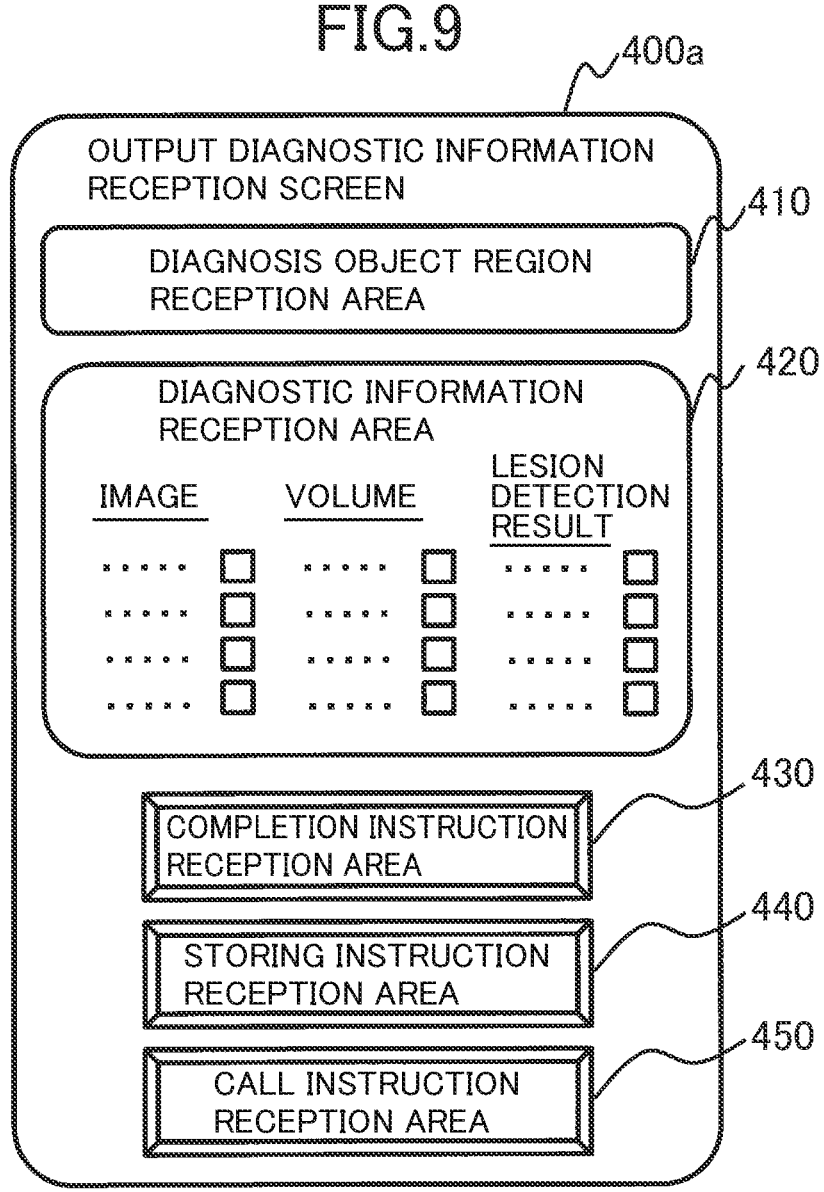
FIG. 9 is an explanatory diagram showing an exemplary output diagnostic information reception screen according to a second modification of the first embodiment hereof.

In order to implement this function, the output diagnostic information reception portion 221 generates a display screen 400a and displays the display screen at the display unit 111. As shown in FIG. 9, the display screen 400a includes: a storing instruction reception area 440 and a call instruction reception area 450, in addition to the diagnosis object region reception area 410, the diagnostic information reception area 420 and the completion instruction reception area 430.

The storing instruction reception area 440 is an area to receive an instruction to store, as the output list, the received output diagnostic information in the information storage portion 225. Further, the call instruction reception area 450 is an area to receive an instruction to call up the stored output list from the information storage portion 225.

Upon receiving an instruction via the storing instruction reception area 440, the output diagnostic information reception portion 221 stores, as the output list, in the information storage portion 225, the set of diagnostic information received via the diagnostic information reception area 420 on the diagnosis object region presently received via the diagnosis object region reception area 410. When the output list is stored, each output list is affixed with identification information (e.g., diagnostic information set name) for identification thereof and stored in the information storage portion 225. The output list is stored on a region-by-region basis.

Upon receiving a call instruction via the call instruction reception area 450, the output diagnostic information reception portion 221 displays the output list stored in the information storage portion 225 in the diagnostic information reception area 420 in a manner to permit selection. At this time, the output diagnostic information reception portion 221 extracts only the output list registered in correspondence to the region received by the diagnosis object region reception area 410 from among the output lists stored in the information storage portion 225, and displays the extraction result.

The output diagnostic information reception portion 221 displays the output list in the diagnostic information reception area 420 of the output diagnostic information reception screen, and receives an instruction for the output diagnostic information by receiving the selection of the output list in question.

Such a configuration permits the user to readily call up and set the diagnostic information list previously generated with respect to the corresponding diagnostic object region, thus reducing the time and effort expended by the user to set the diagnostic information.

<<Second Embodiment>>

Next, description is made on a second embodiment of the present invention. According to this embodiment, the output information reception portion 211 has a function to receive the adjustment of the function and variable used for the calculation of the diagnostic information. Similarly to the first embodiment, the second embodiment is also described by way of example where the MRI apparatus is used as the medical image acquisition apparatus.

Figure 10:
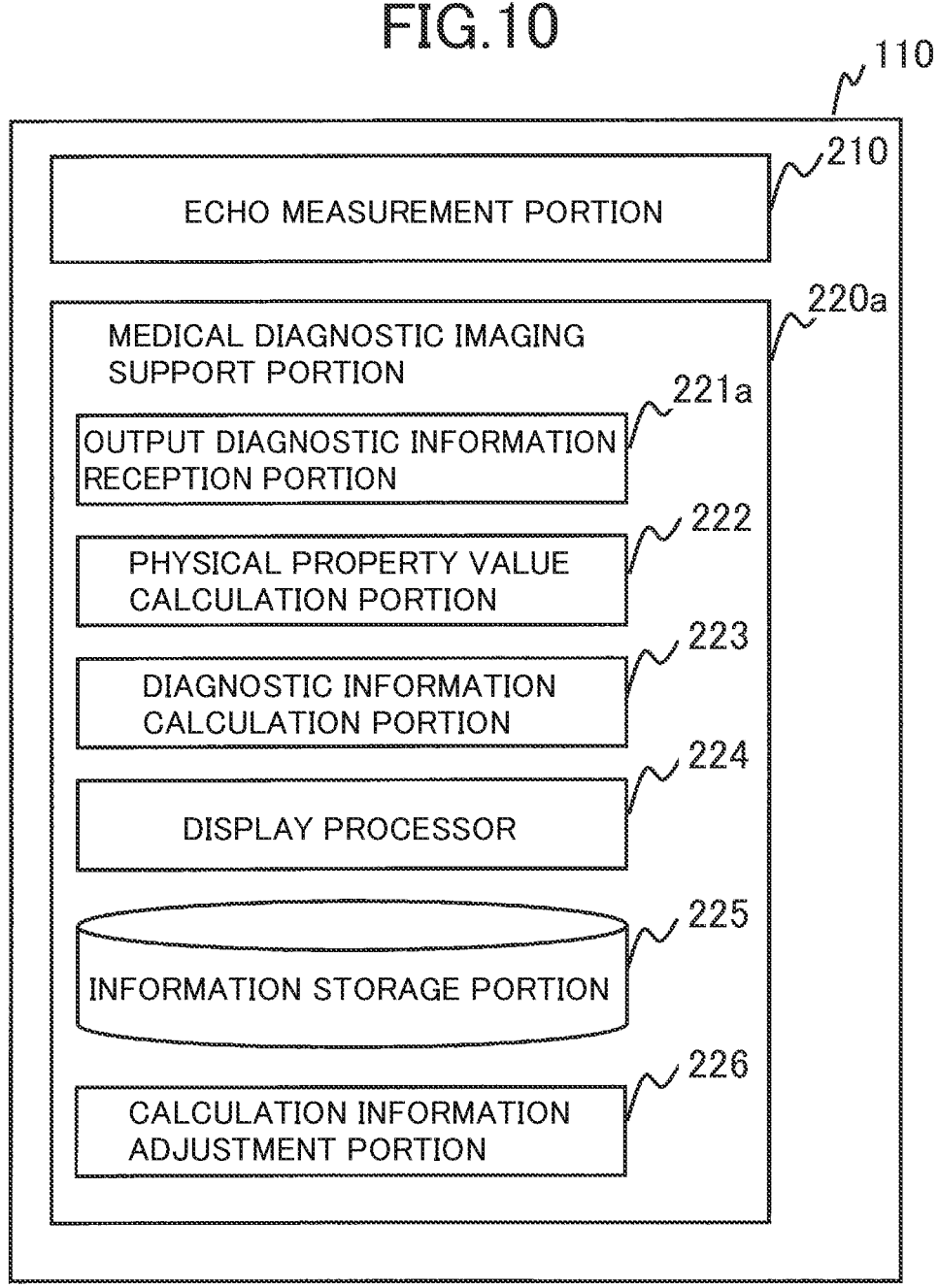
FIG. 10 is a functional block diagram of a computing machine according to a second embodiment of the present invention.

The MRI apparatus of this embodiment has basically the same configuration as the MRI apparatus 100 of the first embodiment. In order to implement the above function, however, a medical diagnostic imaging support portion 220a of this embodiment includes a calculation information adjustment portion 226 for adjusting the calculation information, as shown in FIG. 10. Further, an output diagnostic information reception screen 400b generated by an output diagnostic information reception portion 221a of this embodiment has a different configuration. The following description is made focusing on different components from those of the first embodiment.

The output diagnostic information reception portion 221 of this embodiment also generates the output diagnostic information reception screen as an interface for receiving specified output diagnostic information from the user, and receives the diagnosis object region and the output diagnostic information via the screen in question, similarly to that of the first embodiment.

Figure 11:
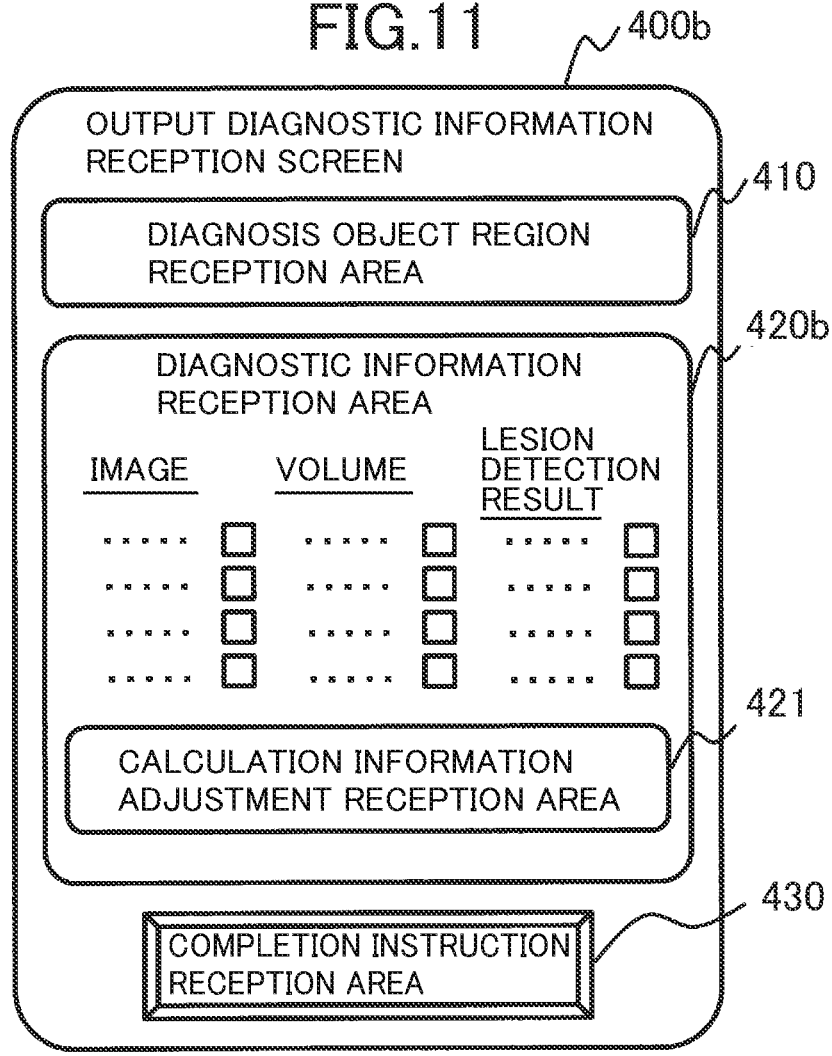
FIG. 11 is an explanatory diagram showing an exemplary output diagnostic information reception screen according to the second embodiment hereof.

FIG. 11 shows an exemplary output diagnostic information reception screen 400b generated by the output information reception portion 211 of this embodiment. As shown in the figure, the output diagnostic information reception screen 400b includes: the diagnosis object region reception area 410 for receiving the diagnosis object region; a diagnostic information reception area 420b for setting the output diagnostic information; and the completion instruction reception area 430 for receiving the input completion instruction.

As described above, the output diagnostic information reception portion 221 of this embodiment receives adjustment of the function and variable for use in the calculation of the diagnostic information. Therefore, the diagnostic information reception area 420b of this embodiment further includes a calculation information adjustment reception area 421 for receiving an adjustment instruction to adjust the function and variable (calculation information) for use in the calculation of the diagnostic information.

The diagnosis object region reception area 410 and the completion instruction reception area 430 are configured the same way as the corresponding components of the first embodiment. Further, the diagnostic information reception area 420b basically has the same configuration as the corresponding component of the first embodiment.

Figure 12:
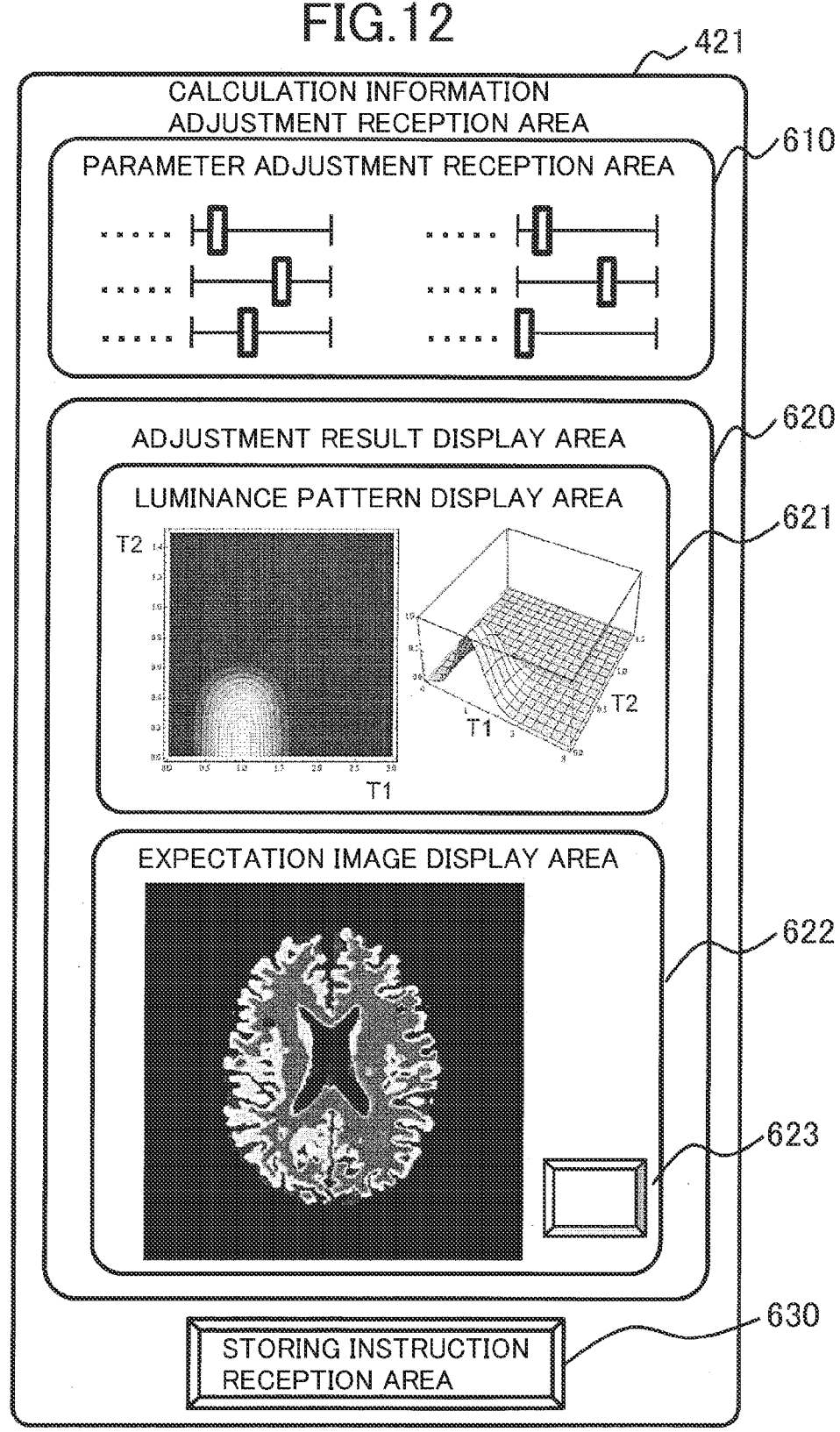
FIG. 12 is an explanatory chart showing an exemplary calculation information adjustment reception area according to the second embodiment hereof.

FIG. 12 shows the details of the calculation information adjustment reception area 421. The calculation information adjustment reception area 421 of this embodiment includes: a parameter adjustment reception area 610; an adjustment result display area 620; and a storing instruction reception area 630. The adjustment result display area 620 includes at least one of a luminance pattern display area 621 for displaying a luminance pattern for the physical property value, and an expectation image display area 622 for displaying a standard image of a diagnosis object region.

The parameter adjustment reception area 610 of the calculation information adjustment reception area 421 receives an adjustment instruction of the calculation information. This figure illustrates a case where an adjustment of the function and variable value for the calculation of luminance value of the image, out of the calculation information, is received. The function and variable for the calculation of luminance value of the image are luminance function and variable of an image based on input of physical property value.

The output diagnostic information reception portion 221 calls up the function stored in advance in the information storage portion 225, such as Sine function, Cosine function, exponent function, logarithm function, Gaussian function, sigmoid function and asymmetrical dual sigmoid function, and presents a changeable function to the user. At this time, the diagnostic information reception portion 221 also presents an inputtable physical property value and a changeable variable to the user. The user can specify the physical property value and adjust the variable via the display.

The adjustment result display area 620 displays the result of a received adjustment each time the adjustment of the variable and/or function is received via the parameter adjustment reception area 610. The calculation information adjustment portion 226 performs the adjustment calculation.

Specifically, the calculation information adjustment portion 226 determines a display mode after adjustment each time the adjustment instruction is received via the parameter adjustment reception area 610, and displays the adjustment result at the adjustment result display area 620. The calculation information adjustment portion 226 calculates, as the display mode after adjustment, at least one of the luminance pattern and the standard image of the diagnosis object region, and displays the result at the adjustment result display area 620.

The luminance pattern display area 621 of the adjustment result display area 620 is an area for real-time display of the luminance variations of an image as mapped to variables of particular input physical property values, the variables received via the parameter adjustment reception area 610. FIG. 12 illustrates a case where the particular input physical property values are T1 and T2. Each time the physical property value and variable are received via the parameter adjustment reception area 610, the calculation information adjustment portion 226 calculates the luminance variation of the image and displays the calculation results as a map.

The calculation information adjustment portion 226 may also be configured for simultaneous display of the physical property value of each tissue located on the above map. In a case where an operator wants to view some tissue, this approach is advantageous in that the operator can easily adjust the variable on the map.

The expectation image display area 622 of the adjustment result display area 620 is an area where a standard image of a diagnosis object region specified via the diagnosis object region reception area 410 is displayed with an outputted contrast. The standard image is stored in advance in the storage unit 112. Each time the input physical property value and variable are received via the parameter adjustment reception area 610, the calculation information adjustment portion 226 generates and displays an image with the outputted contrast.

The expectation image display area 622 may be configured to be switched to a standard image generated from images of plural persons, an image of a single examinee, or a typical image per disease. In this case, the adjustment result display area 620 (the expectation image display area 622) includes, for example, an image switching instruction button 623 as a switching instruction reception area for receiving an instruction to switch the display image.

Upon receiving the instruction to switch the display image via the image switching instruction button 623, the calculation information adjustment portion 226 extracts an image from the storage unit 112 and displays the extracted image with the contrast concerned. The image to be displayed at the expectation image display area 622 is stored in advance in the storage unit 112.

The storing instruction reception area 630 receives a storing instruction. Upon receiving the storing instruction from the user via the storing instruction reception area 630, the output diagnostic information reception portion 221*a* stores the function and variable presently received via the parameter adjustment reception area 610.

The adjusted function and variable are stored in the information storage portion 225 in correspondence to the diagnostic information name. The adjusted function and variable may be overwritten on the function and variable before adjustment which are stored in correspondence to the diagnostic information name. Otherwise adjusted function and variable may be stored in correspondence to a different diagnostic information name.

By selecting the diagnostic information name, the user can call up the previously stored function and variable for the calculation of diagnostic information from the information storage portion 225. The user can make new adjustment to the retrieved function and variable, and store the resultant function and variable in the information storage portion 225 again.

The processing after the selection of the output diagnostic information is the same as that of the first embodiment.

The MRI apparatus 100 of this embodiment includes the echo measurement portion 210 and the medical diagnostic imaging support portion 220, similarly to that of the first embodiment. The medical diagnostic imaging support portion 220 includes: the output diagnostic information reception portion 221; the physical property value calculation portion 222; the diagnostic information calculation portion 223; the display processor 224; and the information storage portion 225. The medical diagnostic imaging support portion 220 of this embodiment further includes the calculation information adjustment portion 226 for adjusting the calculation information. The output diagnostic information reception screen 400*b* generated by the output diagnostic information reception portion 221 further includes the calculation information adjustment reception area 421 for receiving the instruction to adjust the calculation information.

As described above, this embodiment has the same configuration as the first embodiment. Therefore, this embodiment can afford the same effects as the first embodiment.

Further, the embodiment is adapted for free adjustment of the calculation information used for the generation of diagnostic information. According to this embodiment, therefore, the user can adjust the image contrast in any emphasis pattern without being restricted by the pulse sequence or imaging parameter.

The embodiment includes the adjustment result display area for displaying the adjustment result during the adjustment operation. Hence, the user can make adjustment while viewing the adjustment result. Accordingly, the user can generate an arbitrary emphasized image as desired. Further, the user can acquire a desired image without making WL/WW adjustment.

In the adjustment result display area, an image with the adjusted contrast is displayed as an expectation image. Therefore, the user can adjust the luminance pattern according to tissue as the object. At this time, the user can switch the display image to any of the various types. Hence, the user can set the image contrast not only to a healthy subject but also to a disease case. For example, the image can be adjusted to a contrast specialized in a particular disease so that an improved diagnostic performance is achieved.

According to the embodiment as described above, the improvement in operability and diagnostic performance can be expected.

It is noted that the modifications of the first embodiment are also applicable to this embodiment.

<<Third Embodiment>>

Next, description is made on a third embodiment of the present invention. According to this embodiment, a pulse sequence capable of fastest acquisition of a physical property value necessary for input of user-specified diagnostic information is automatically generated.

An MRI apparatus of this embodiment has basically the same configuration as the MRI apparatus 100 of the first embodiment. In order to implement the above function, however, a medical diagnostic imaging support portion 220*c* of this embodiment has a different configuration. The following description is made, focusing on the difference from the first embodiment.

Figure 13:
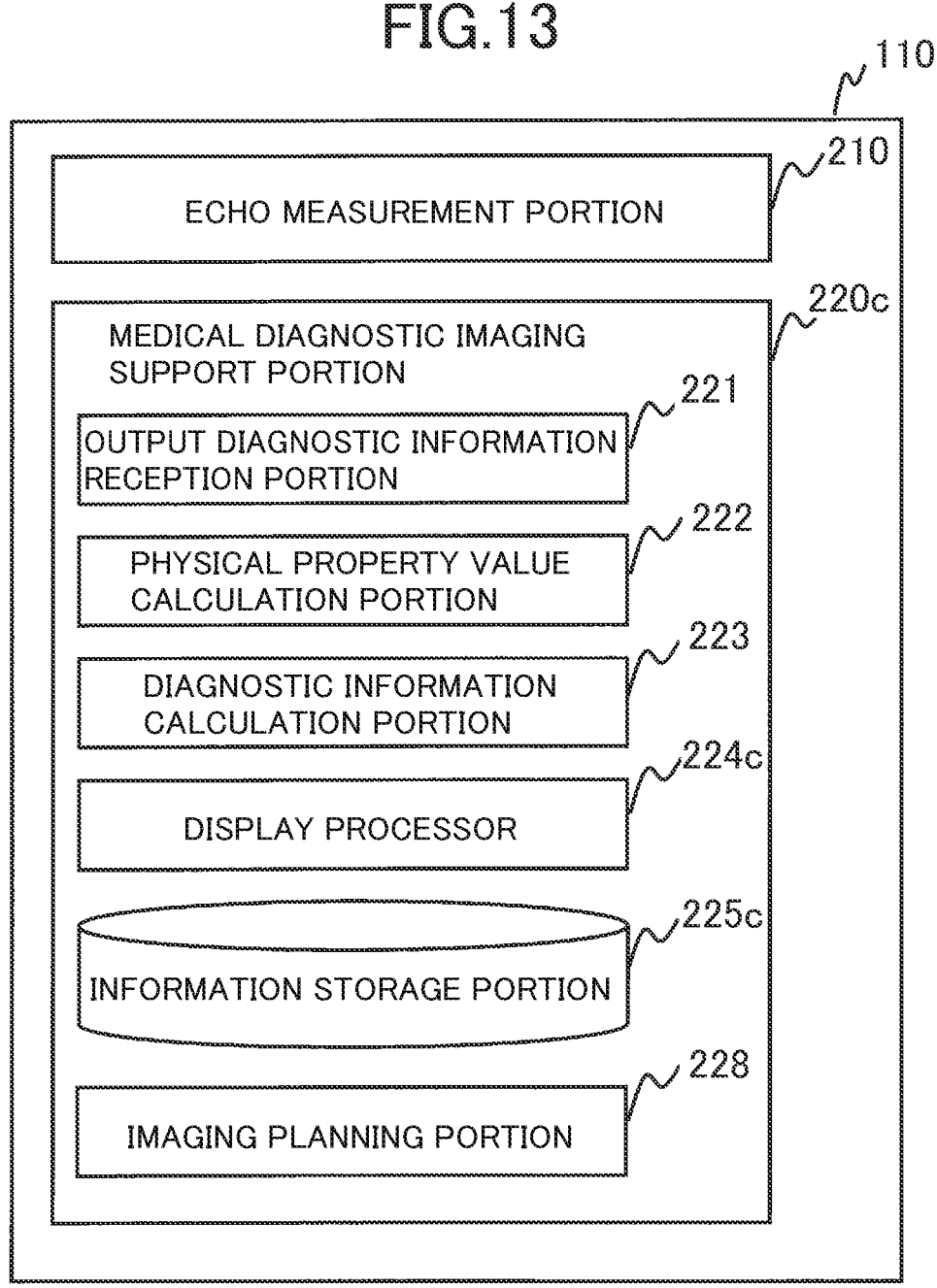
FIG. 13 is a functional block diagram of a computing machine according to a third embodiment of the present invention.

In order to accomplish the automatic generation of the pulse sequence, the medical diagnostic imaging support portion 220*c* of this embodiment includes an imaging planning portion 228 in addition to the components of the medical diagnostic imaging support portion 220 of the first embodiment, as shown in FIG. 13. Further, data stored in an information storage portion 225*c* also differs. Furthermore, a display processor 224*c* also performs different operations.

As shown in FIG. 14, the information storage portion 225*b* of this embodiment stores, for each diagnostic information name 301, imaging information 304 in addition to the input physical property value 302 and the calculation information 303. The imaging information 304 is a list of a pulse sequence (measurement method) capable of acquiring at least one of the diagnostic information name 301 and the input physical property value 302, and time related to the pulse sequence.

Further, this embodiment determines whether or not the calculation of physical property value is necessary. Therefore, information indicating whether or not the calculation of physical property value is necessary in the calculation of the diagnostic information name 301 is also stored.

Based on the imaging information 304 stored in the information storage portion 225, the imaging planning portion 228 generates a set of pulse sequences capable of fastest acquisition of the input physical property value 302 as an optimum imaging (protocol). Subsequently, the imaging planning portion presents the resultant protocol to the user.

In a case where a plurality of output diagnostic information items are specified by the user, the imaging planning portion 228 plans an imaging operation by selecting a pulse sequence capable of fastest acquisition of all the input physical property values necessary for the calculation of the plural output diagnostic information items.

The imaging planning portion 228 of this embodiment determines whether or not the calculation of the physical property value is necessary for the specified output diagnostic information item, and informs the display processor 224 of the determination result.

As shown in FIG. 14, for example, it is assumed that T1 value, T2 value and PD as the input physical property values; and computable measurement methods which include T1-weighted imaging sequence (T1 WS; measurement time 3 min.) capable of acquiring the T1-weighted image per se as the diagnostic information, and T1 value, T2 value, PD and B1 simultaneous measurement pulse sequence (SWS; 5 min.) capable of acquiring all the input physical property values are stored in the information storage portion 225*b* in correspondence to the diagnostic information name "T1-weighted image". In this case, if T1 WS is used, the calculation of the physical property value is written as "unnecessary" because the calculation of the physical property value is not needed. If SWS is used, on the other hand, the calculation of the physical property value is written as "necessary" because the calculation of the physical property value is needed.

It is further assumed that T1 value, T2 value and PD as the input physical property values; and the computable measurement methods which include T2-weighted imaging sequence (T2 WS; measurement time 3 min.) capable of acquiring the T2-weighted image per se, and the T1 value, T2 value, PD and B1 simultaneous measurement pulse sequence (SWS; 5 min.) capable of acquiring all the input physical property values are stored in correspondence to the diagnostic information name "T2 -weighted image". In this case as well, the necessity of the calculation of the physical property value is described the same way as the above.

It is further assumed that T1 value, T2 value and PD as the input physical property values; and the computable measurement methods which include FLAIR weighted imaging sequence (FWS; measurement time 3 min.) capable of acquiring FLAIR image per se, and the T1 value, T2 value, PD and B1 simultaneous measurement pulse sequence (SWS; 5 min.) capable of acquiring all the input physical property values are stored in correspondence to the diagnostic information name "FLAIR".

In a case where the output diagnostic information reception portion 221 receives only the T1-weighted image as the diagnostic information type, the imaging planning portion 228 extracts from the information storage portion 225 b the input physical property value and the measurement method registered in correspondence to the T1-weighted image. Then, the imaging planning portion decides the necessary physical property value and the imaging sequence capable of achieving the fastest measurement. In this case, the T1-weighted imaging sequence is selected as the imaging sequence. The imaging planning portion 228 generates the protocol according to the T1-weighted pulse sequence.

In this case, the execution of the T1-weighted imaging sequence enables the acquisition of the T1-weighted image without calculating the physical property value. Therefore, the imaging planning portion 228 determines that the calculation of the physical property value is unnecessary.

On the other hand, in a case where the output diagnostic information reception portion 221 receives, as the output diagnostic information, the output diagnostic information types which include the T1-weighted image, T2-weighted image and FLAIR image, two protocols are conceivable which include: a first protocol where T1 WS, T2 WS and FWS are executed, respectively, without calculating the physical property value; and a second protocol where only SWS is executed for calculating the physical property values of T1 value, T2 value and PD, and respective images are generated from the physical property values. The first protocol takes 9 minutes in total, while the second protocol takes 5 minutes in total.

In this case, the imaging planning portion 228 generates the protocol based on the pulse sequence for simultaneous measurement of T1-value, T2-value, PD and B1. Further, the imaging planning portion determines that the calculation of the physical property value is unnecessary.

In the case where it is determined that the calculation of the physical property value is unnecessary, the display processor 224*b* reconstructs the echo signal acquired by executing the imaging sequence and displays the resultant signal at the image display area 510 of the display screen.

Figure 15:
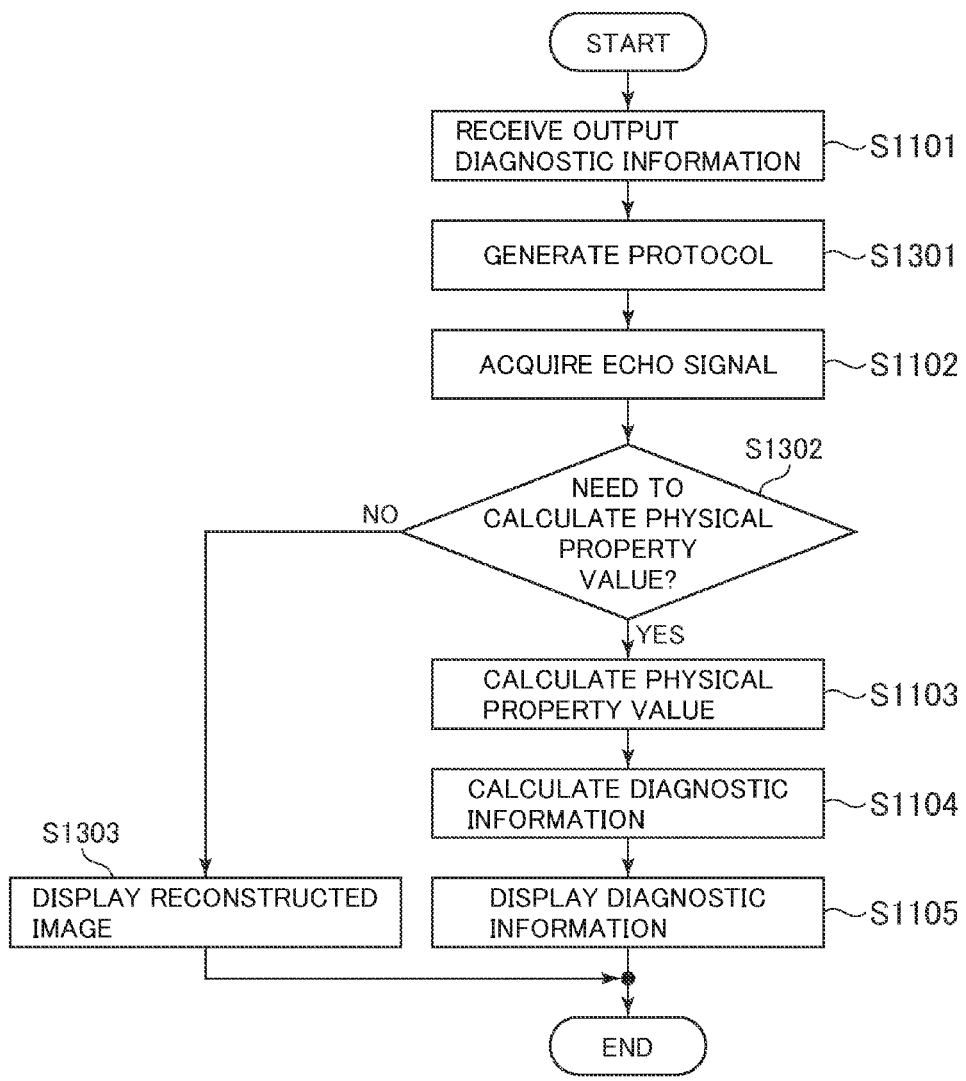
FIG. 15 is a flow chart showing the steps of a diagnostic information calculation process according to the third embodiment hereof.

A flow of diagnostic information calculation process performed by individual components of the computing machine 110 of this embodiment is described as below. FIG. 15 is a flow chart showing the steps of the diagnostic information calculation process according to this embodiment.

First, the user selects a desired type of diagnostic information via the output diagnostic information reception screen 400. The output diagnostic information reception portion 221 receives the user-selected diagnostic information type as the output diagnostic information (Step S1101). The output diagnostic information is stored in the information storage portion 225.

Next, the imaging planning portion 228 generates a protocol including a set of pulse sequences capable of the fastest measurement of the user-specified diagnostic information type and presents the protocol to the user (Step S1301). At this time, the imaging planning portion 228 also determines whether the calculation of physical property value is necessary or not.

Next, in response to an imaging instruction from the user, the echo measurement portion 210 acquires an echo signal by controlling the pulse sequences according to the protocol generated in Step S1301 (Step S1102).

If it is determined in Step S1301 that the calculation of the physical property value is unnecessary (Step S1302), the display processor 224*c* displays at the display unit 111 an image acquired by reconstructing the echo signals acquired at Step S1102 (Step S1303). Subsequently, the display processor terminates the process.

On the other hand, if it is determined that the calculation of the physical property value is necessary, the physical property value calculation portion 222 calculates the physical property value from the acquired echo signal (Step S1103).

Next, the diagnostic information calculation portion 223 refers to the information storage portion 225 and calculates the output diagnostic information selected at Step S1101 by using the calculated physical property value (Step S1104).

Finally, the display processor 224*c* displays the calculated output diagnostic information at the display unit 111 (Step S1105), and terminates the process.

Similarly to the first embodiment, the MRI apparatus 100 of this embodiment includes as described above: the echo measurement portion 210 and the medical diagnostic imaging support portion 220. The medical diagnostic imaging support portion 220 includes: the output diagnostic information reception portion 221; the physical property value calculation portion 222; the diagnostic information calculation portion 223; the display processor 224; and the information storage portion 225. The medical diagnostic imaging support portion 220 of this embodiment further includes the imaging planning portion which plans the optimum imaging for acquiring all the input physical property values required for the calculation of the output diagnostic information received.

As described above, this embodiment has the same configuration as the first embodiment. Therefore, this embodiment can provide the same effects as the first embodiment.

Further, this embodiment automatically generates the protocol capable of fastest calculation of the output diagnostic information. The user can acquire the diagnostic information via the efficient examination protocol simply by specifying a desired diagnostic information type. Therefore, the time and effort expended by the user are reduced, which leads to the improvement of the examination efficiency.

It is noted that all the modifications of the first embodiment are also applicable to this embodiment. Similarly to the second embodiment, the calculation information may be made adjustable. Further, the modification of the second embodiment is also applicable to this embodiment.

<Modification>

Figure 16:
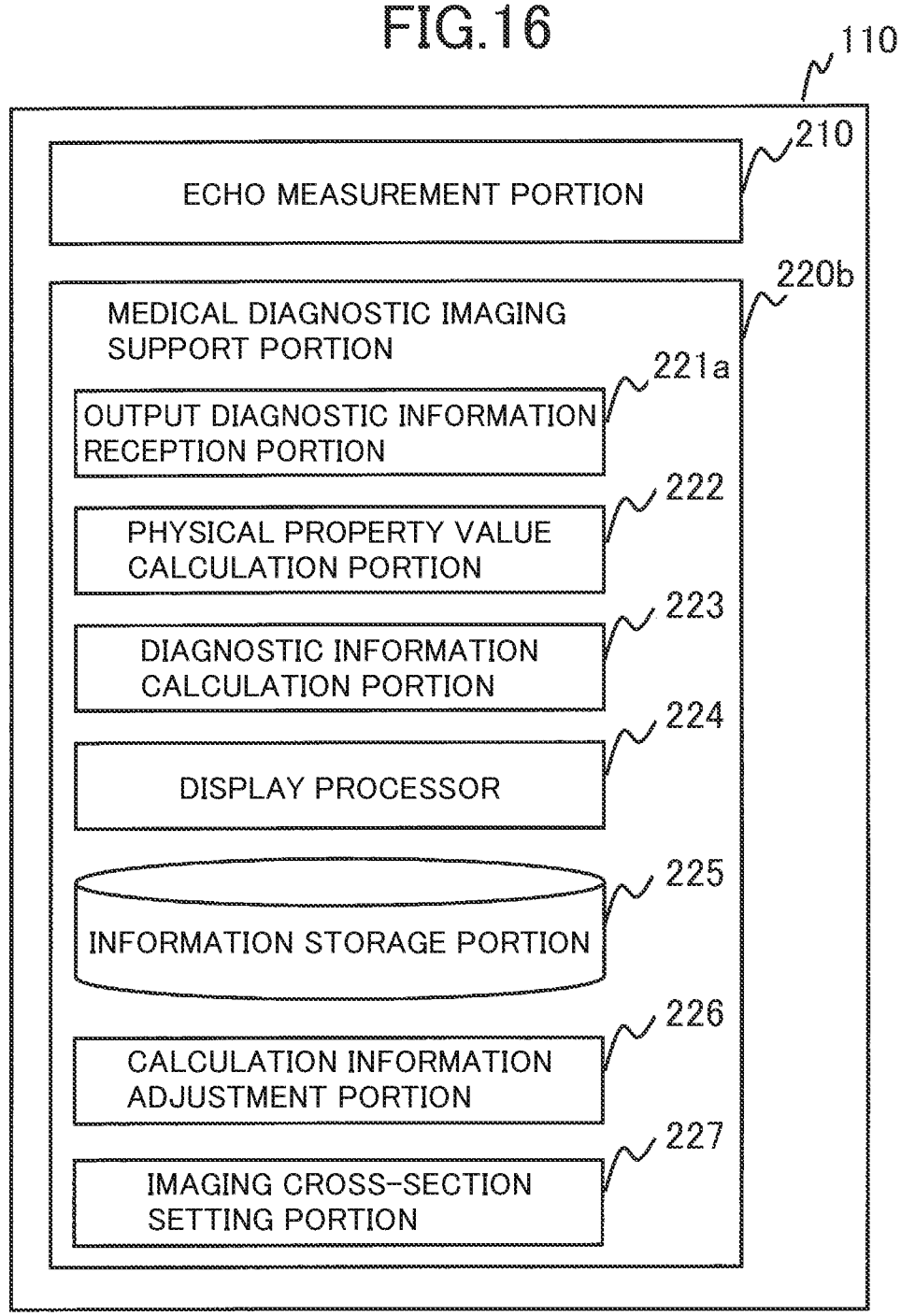
FIG. 16 is a block diagram showing a computing machine according to a modification of the embodiment of the present invention.

As shown in FIG. 16, a medical diagnostic imaging support portion 220b of each of the above embodiments may further include an imaging cross-section setting portion 227 for automatically setting an imaging position.

In this case, an output diagnostic information reception screen 400c further includes, as shown in FIG. 17, an imaging cross-section position reception area 440 for receiving an approximate position of an automatically set imaging cross-section as specified by the user.

The imaging cross-section setting portion 227 calculates and sets the imaging cross-section based on the designation received via the imaging cross-section position reception area 440. Any of the known methods may be used for the setting. In a case where the user specifies an imaging cross-section position based on the OM line, for example, a method may be adopted which includes the steps of: capturing a 3D scout image; extracting the OM line by automatically recognizing anatomical features; and setting the imaging position.

This modification negates the need for a positioning operation by the user at the time of image capturing or the need for an operation of segmenting cross-sections of the image after the image capturing. This leads to further improvement in operability.

The computing machine 110 of each of the above embodiments may be configured as an independent diagnostic support apparatus which is separate from the control of the sequencer 104 in the MRI apparatus 100 and adapted to exclusively receive the echo signal or image from the storage unit 112. This configuration permits the diagnostician to acquire desired diagnostic information via a cloud service even where there is no MRI apparatus.

While the foregoing embodiments have been described by way of example where the MRI apparatus is used as the medical image acquisition apparatus, the medical image acquisition apparatus is not limited to the MRI apparatus. For example, the medical image acquisition apparatus may be a CT apparatus, an ultrasonic diagnostic apparatus or the like. The CT apparatus is capable of measurement of CT value as the physical property value. The ultrasonic diagnostic apparatus is capable of measurement of elastic modulus as the physical property value. The embodiments of the present invention are not limited to the foregoing embodiments, and a variety of modifications or changes may be made thereto without departing from the spirits of the present invention.

LIST OF REFERENCE SIGNS

100: MRI APPARATUS, 101: MAGNET, 102: GRADIENT MAGNETIC FIELD COIL, 103: TEST SUBJECT, 104: SEQUENCER, 105: GRADIENT MAGNETIC FIELD POWER SUPPLY, 106: HIGH-FREQUENCY MAGNETIC FIELD GENERATOR, 107: RF COIL, 108: RF PROBE, 109: RECEIVER, 110: COMPUTING MACHINE, 111: DISPLAY UNIT, 112: STORAGE UNIT, 113: SHIM COIL, 114: SHIM POWER SUPPLY, 115: TABLE, 116: INPUT DEVICE, 210: ECHO MEASUREMENT PORTION, 211: OUTPUT INFORMATION RECEPTION PORTION, 220: MEDICAL DIAGNOSTIC IMAGING SUPPORT PORTION, 220a: MEDICAL DIAGNOSTIC IMAGING SUPPORT PORTION, 220b: MEDICAL DIAGNOSTIC IMAGING SUPPORT PORTION, 220c: MEDICAL DIAGNOSTIC IMAGING SUPPORT PORTION, 221: OUTPUT DIAGNOSTIC INFORMATION RECEPTION PORTION, 221a: OUTPUT DIAGNOSTIC INFORMATION RECEPTION PORTION, 222: PHYSICAL PROPERTY VALUE CALCULATION PORTION, 223: DIAGNOSTIC INFORMATION CALCULATION PORTION, 224: DISPLAY PROCESSOR, 224b: DISPLAY PROCESSOR, 224c: DISPLAY PROCESSOR, 225: INFORMATION STORAGE PORTION, 225b: INFORMATION STORAGE PORTION, 225c: INFORMATION STORAGE PORTION, 226: CALCULATION INFORMATION ADJUSTMENT PORTION, 227: IMAGING CROSS-SECTION SETTING PORTION, 228: IMAGING PLANNING PORTION, 301: DIAGNOSTIC INFORMATION NAME, 302: INPUT PHYSICAL PROPERTY VALUE, 303: CALCULATION INFORMATION, 304: IMAGING INFORMATION, 400: OUTPUT DIAGNOSTIC INFORMATION RECEPTION SCREEN, 400a: OUTPUT DIAGNOSTIC INFORMATION RECEPTION SCREEN, 400b: OUTPUT DIAGNOSTIC INFORMATION RECEPTION SCREEN, 400c: OUTPUT DIAGNOSTIC INFORMATION RECEPTION SCREEN, 410: DIAGNOSIS OBJECT REGION RECEPTION AREA, 420: DIAGNOSTIC INFORMATION RECEPTION AREA, 420b: DIAGNOSTIC INFORMATION RECEPTION AREA, 421: CALCULATION INFORMATION ADJUSTMENT RECEPTION AREA, 430: COMPLETION INSTRUCTION RECEPTION AREA, 440: IMAGING CROSS-SECTION POSITION RECEPTION AREA 440: STORING INSTRUCTION RECEPTION AREA, 450: CALL INSTRUCTION RECEPTION AREA, 500: DISPLAY SCREEN, 500a: DISPLAY SCREEN, 510: IMAGE DISPLAY AREA, 520: VOLUME DISPLAY AREA, 530: LESION DETECTION RESULT DISPLAY AREA, 540: DIAGNOSTIC INFORMATION RECEPTION AREA, 610: PARAMETER ADJUSTMENT RECEPTION AREA, 620: ADJUSTMENT RESULT DISPLAY AREA, 621: LUMINANCE PATTERN DISPLAY AREA, 622: EXPECTATION IMAGE DISPLAY AREA, 623: IMAGE SWITCHING INSTRUCTION BUTTON, 630: STORING INSTRUCTION RECEPTION AREA

The invention claimed is:

1. A medical diagnostic imaging support apparatus comprising:
   a memory configured to store a plurality of types of diagnostic information in correspondence with a plurality of predetermined physical property values, a plurality of predetermined equations, and a plurality of predetermined values of variables of each of the predetermined equations; and
   a processor programmed by executable instructions in the memory to perform operations including:
   displaying a diagnostic information reception area;
   receiving, via the diagnostic information reception area, a selection of diagnostic information to be output from among the plurality of types of diagnostic information;

calculating, upon receiving the selected diagnostic information via the diagnostic information reception area and receiving the measurement data acquired by a medical image acquisition apparatus, the predetermined physical property values corresponding to the selected diagnostic information from the measurement data acquired by the medical image acquisition apparatus by fitting the measurement data to a predetermined signal function and estimating the physical property values as variables of the signal function;

calculating the selected diagnostic information by using the calculated physical property values and one of the predetermined equations and the predetermined values of variables of the one of the predetermined equations corresponding to the selected diagnostic information; and generating a display screen from the calculated diagnostic information and displaying the resultant display screen.

2. The medical diagnostic imaging support apparatus according to claim 1,
wherein the medical image acquisition apparatus is a magnetic resonance imaging apparatus, and
the measurement data is an echo signal.

3. The medical diagnostic imaging support apparatus according to claim 1,
wherein the types of diagnostic information include at least one of an image based on a physical property value of living tissue, a volume of a predetermined area, and a lesion detection result, and
the display screen includes a display area for each of the types of diagnostic information.

4. The medical diagnostic imaging support apparatus according to claim 1, wherein the processor is further programmed by the executable instructions in the memory to perform operations including:
adjusting the one of the predetermined equations corresponding to the selected diagnostic information to another one of the predetermined equations,
wherein the diagnostic information reception screen further includes a calculation information adjustment reception area for receiving an instruction to adjust the one of the predetermined equations.

5. The medical diagnostic imaging support apparatus according to claim 4,
wherein the calculation information adjustment reception area further includes an adjustment result display area for displaying an adjustment result, and
at each reception of the adjustment instruction, display mode after adjustment is displayed at the adjustment result display area.

6. A medical diagnostic imaging support apparatus comprising:
a memory configured to store a plurality of types of diagnostic information in correspondence with a plurality of predetermined physical property values, a plurality of predetermined equations, a plurality of predetermined values of variables of each of the predetermined equations, and a plurality of pulse sequences and time values thereof; and
a processor programmed by executable instructions in the memory to perform operations including:
receiving a selection of diagnostic information to be output from among the plurality of types of diagnostic information;
generating a set of the pulse sequences corresponding to the selected diagnostic information to be applied by a medical image acquisition apparatus for acquiring all of the physical property values required to calculate the selected diagnostic information;

calculating, upon receiving measurement data acquired by the medical image acquisition apparatus applying the generated set of the pulse sequences, the predetermined physical property values corresponding to the selected diagnostic information from the measurement data acquired by the medical image acquisition apparatus by fitting the measurement data to a predetermined signal function and estimating the physical property values as variables of the signal function;

calculating the selected diagnostic information by using the calculated physical property values and one of the predetermined equations and the predetermined values of variables of the one of the predetermined equations corresponding to the selected diagnostic information; and generating a display screen from the calculated diagnostic information and displaying the resultant display screen.

7. A medical diagnostic imaging support apparatus comprising:
a memory configured to store a plurality of types of diagnostic information in correspondence with a plurality of predetermined physical property values, a plurality of predetermined equations, and a plurality of predetermined values of variables of each of the predetermined equations; and
a processor programmed by executable instructions in the memory to perform operations including:
displaying a diagnostic information reception screen including a diagnostic information reception area for selecting the diagnostic information;
receiving, via the diagnostic information reception screen, a selection of diagnostic information to be output from among the plurality of types of diagnostic information;
calculating, upon receiving the selected diagnostic information via the diagnostic information reception screen and receiving the measurement data acquired by a the medical image acquisition apparatus, the predetermined physical property values corresponding to the selected diagnostic information from the measurement data acquired by the medical image acquisition apparatus by fitting the measurement data to a predetermined signal function and estimating the physical property values as variables of the signal function;
calculating the selected diagnostic information by using the calculated physical property values and one of the predetermined equations and the predetermined values of variables of the one of the predetermined equations corresponding to the selected diagnostic information; and
generating a display screen from the calculated diagnostic information and displaying the resultant display screen,
wherein the output diagnostic information reception screen includes:
a storing instruction reception area for receiving an instruction to store the selected diagnostic information as an output list; and
a call instruction reception area for displaying the stored output list, and
wherein the processor is further programmed by the executable instructions in the memory to perform operations including:
storing, as the output list, the selected diagnostic information received via the storing instruction reception area, and displaying, via the call instruction reception area, the stored output list at the diagnostic information reception area.

8. The medical diagnostic imaging support apparatus according to claim 5,
wherein the processor is further programmed by the executable instructions in the memory to perform operations including: calculation information adjustment portion calculates at least one of a luminance pattern and a standard image of a diagnosis object region, as the display mode after adjustment, and displays the calculation result at the adjustment result display area.

9. The medical diagnostic imaging support apparatus according to claim 8,
wherein in a case where the standard image is displayed at the adjustment result display area, the adjustment result display area includes a switching instruction reception area for receiving an instruction to switch the displayed image to any one of an image generated from data of plural individuals, an image of one typical test subject, and an image of disease case.

10. The medical diagnostic imaging support apparatus according to claim 6,
wherein
the set of the pulse sequences are generated as an optimum imaging for a fastest acquisition of all of the physical property values required to calculate the selected diagnostic information.

11. The medical diagnostic imaging support apparatus according to claim 3,
wherein the image based on a physical property value of living tissue is at least one of emphasized image weighted with a predetermined test subject parameter, physical property value image, segmented image per anatomical tissue, extraction image of abnormal tissue, and structure image.

12. The medical diagnostic imaging support apparatus according to claim 3,
wherein the image based on a physical property value of living tissue is an image of an identifiable structure of a lesion region in question with an overlaid image of a detected lesion region.

13. The medical diagnostic imaging support apparatus according to claim 3,
wherein the image is an image based on a physical property value of living tissue recognizably displaying a character difference of a detected lesion.

14. The medical diagnostic imaging support apparatus according to claim 1,
wherein the diagnostic information includes at least one of the volume of anatomical tissue, the volume of abnormal tissue, the existence probability of anatomical tissue, the existence probability of abnormal tissue, and neoplastic lesion.

15. The medical diagnostic imaging support apparatus according to claim 1, further comprising an imaging cross-section setting portion for setting an imaging cross-section,
wherein the output diagnostic information reception portion includes an imaging cross-section position reception area for receiving the designation of an approximate position of the imaging cross-section, and
the imaging cross-section setting portion calculates and sets the imaging cross-section based on the designation received via the imaging cross-section position reception area.

* * * * *